(12) United States Patent
Sittisombut et al.

(10) Patent No.: US 12,098,165 B2
(45) Date of Patent: Sep. 24, 2024

(54) MATURE VIRUS-LIKE PARTICLES OF FLAVIVIRUSES

(71) Applicants: Chiang Mai University, Chiang Mai (TH); National Science and Technology Development Agency (NSTDA), Pathum Thani (TH)

(72) Inventors: Nopporn Sittisombut, Chiang Mai (TH); Malinee Sae-Lim, Chiang Mai (TH); Nicha Charoensri, Chiang Mai (TH); Poonsook Keelapang, Chiang Mai (TH)

(73) Assignees: Chiang Mai University, Chiang Mai (TH); National Science and Technology Development Agency (NSTDA), Pathum Thani (TH)

( * ) Notice: Subject to any disclaimer, the term of this patent is extended or adjusted under 35 U.S.C. 154(b) by 735 days.

(21) Appl. No.: 17/262,327

(22) PCT Filed: May 28, 2019

(86) PCT No.: PCT/TH2019/000015
§ 371 (c)(1),
(2) Date: Jan. 22, 2021

(87) PCT Pub. No.: WO2020/242388
PCT Pub. Date: Dec. 3, 2020

(65) Prior Publication Data
US 2021/0324013 A1    Oct. 21, 2021

(51) Int. Cl.
| C07K 14/005 | (2006.01) |
| A61K 39/00 | (2006.01) |
| A61K 39/12 | (2006.01) |
| A61P 31/14 | (2006.01) |
| C12N 7/00 | (2006.01) |

(52) U.S. Cl.
CPC ............ *C07K 14/005* (2013.01); *A61K 39/12* (2013.01); *A61P 31/14* (2018.01); *C12N 7/00* (2013.01); *A61K 2039/5258* (2013.01); *C12N 2770/24122* (2013.01); *C12N 2770/24123* (2013.01); *C12N 2770/24134* (2013.01); *C12N 2770/24171* (2013.01)

(58) Field of Classification Search
CPC .......... C07K 14/005; A61K 39/12; A61K 2039/5258; A61P 31/14; A61P 31/12; C12N 7/00; C12N 2770/24122; C12N 2770/24123; C12N 2770/24134; C12N 2770/24171; Y02A 50/30
See application file for complete search history.

(56) References Cited

U.S. PATENT DOCUMENTS

| 10,117,924 B2 * | 11/2018 | de Silva ............ C12N 7/00 |
| 2019/0374633 A1 * | 12/2019 | Graham ............ G01N 33/536 |

FOREIGN PATENT DOCUMENTS

| WO | 2010103488 A1 | 9/2010 |
| WO | 2016038895 A1 | 3/2016 |

OTHER PUBLICATIONS

Krol et al. (Krol E, Brzuska G, Szewczyk B. Production and Biomedical Application of Flavivirus-like Particles. Trends Biotechnol. Nov. 2019;37(11):1202-1216. Epub Apr. 16, 2019. (Year: 2019).*
Chaudhury et al., "Structure-Based pKa Prediction Provides a Thermodynamic Basis for the Role of Histidines in pH-Induced Conformational Transitions in Dengue Virus," Biochem Biophys Rep., 4:375-385, Oct. 2015.
International Search Report and Written Opinion of the ISA/EP in PCT/TH2019/000015, dated Jan. 23, 2020; 16pgs.
Lloyd, Y.M., "Study of Mature Dengue Virus-Like Particles as New Dengue Vaccine Candidate," Thesis—Master of Science in Tropical Medicine, Graduate Division, University of Hawai'i at Mānoa, Aug. 2014, 91pgs.
Suphatrakul et al., "Generation and Preclinical Immunogenicity Study of Dengue Type 2 Virus-like Particles Derived from Stably Transfected Mosquito Cells," Vaccine, 33(42):5613-5622, Oct. 2015.
Urakami et al., "An Envelope-Modified Tetravalent Dengue Virus-Like-Particle Vaccine Has Implications for Flavivirus Vaccine Design," J Virol., 91(23):e01181-17, Dec. 2017.
Zheng et al., "A Toggle Switch Controls the Low pH-Triggered Rearrangement and Maturation of the Dengue Virus Envelope Proteins," Nat Comm., 5(3877), May 2014, 9pgs.

* cited by examiner

*Primary Examiner* — Rachel B Gill
(74) *Attorney, Agent, or Firm* — Haukaas Fortius PLLC; Paul K. Judd

(57) ABSTRACT

Modified and expressed virus-like particles are described that are capable of eliciting immune response in a mammal upon administrating a pharmaceutically efficient dosage to the mammal. The virus-like particle comprises a modified form of M and E structural proteins of flavivirus. Further, the virus-like particle comprises an amino acids sequence substantially corresponding to a sequence set forth in SEQ ID NO: 1, SEQ ID NO: 2, SEQ ID NO: 3, or SEQ ID NO: 4, wherein conserved and internally located His at multiple positions of the M and E proteins are substituted with uncharged residues, and other secretion-enhancing substitutions are introduced.

11 Claims, 9 Drawing Sheets
Specification includes a Sequence Listing.

SEQ ID NO. 1

```
  1    SVALAPAVGL GLETRTETWM SSEGAWKQIQ RVETWALRHP GFTVIALFLA   50
 51    HAIGTSITQK GIIFILLMLV TPSMAMRCVG IGSRDFVEGL SGATWVDVVL  100
101    ENGSCVTTMA KDKPTLDIEL LKTEVTNPAV LRKLCIEAKI SNTTTDSRCP  150
151    TQGEATLVEE QDANFVCRRT FVDRGWGNGC GLFGKGSLLT CAKFKCVTKL  200
201    EGKIVQYENL KYSVIVTVHT GDQNQVGNES TEHGTTATIT PQAPTTEIQL  250
251    TDYGALTLDC FPLTGLDFNE MVLLTMKEKS WLVNKQWFLD LPLPWTSGAS  300
301    TSQETWNRQD LLVTFKTAHA KKQEVVVLGS QEGAMATALT GATEIQTSGT  350
351    TTIFAGALKC RLKMDKLTLK GMSYVMCTGS FKLEKEVAET QAGTVLVQIK  400
401    YEGTDAPCKI PFSTQDEKGV TQNGRLITAN PIVTDKEKPV NIEAEPPFGE  450
451    SYIVIGAGEK ALKLSWFKKG STLGKAFSTT LKGAQRLAAL GDTAWDFGSI  500
501    GGVFNSIGKA VHQVFGGAFR TLFGGMSWIT QGLMGALLLW MGVNARDRSI  550
551    ALAFLATGGV LVFLATNVHA                                   570
```

Figure 1

SEQ ID NO. 2

```
  1    SVALVPAVGM GLETRTETWM SSEGAWKHAQ RIETWILRHP GFTIMAAILA   50
 51    YTIGTTHFQR VLIFILLTAV APSMTMRCIG ISNRDFVEGV SGGSWVDIVL  100
101    ENGSCVTTMA KNKPTLDFEL IKTEAKQPAT LRKYCIEAKL TNTTTESRCP  150
151    TQGEPSLKEE QDKRFVCKHS MVDRGWGNGC GLFGKGGIVT CAMFTCKKNM  200
201    EGKIVQPENL EYTIVVTPHS GEENAVGNDT GKHGKEIKVT PQSSITEAEL  250
251    TGYGTVTMEC FPLTGLDFNE MVLLQMENKA WLVNRQWFLD LPLPWLPGAD  300
301    KQESNWIQKE TLVTFKSPHA KKQDVVVLGS QEGAMATALT GATEIQMSSG  350
351    NLLFTGALKC RLRMDKLQLK GMSYSMCTGK FKVVKEIAET QAGTIVIQVQ  400
401    YEGDGSPCKI PFEIMDLEKR YVLGRLITVN PIVTEKDSPV NIEAEPPFGD  450
451    SYIIIGVEPG QLKLNWFKKG STLGKAFSTT LKGAQRLAAL GDTAWDFGSI  500
501    GGVFNSIGKA VHQVFGGAFR TLFGGMSWIT QGLMGALLLW MGVNARDRSI  550
551    ALAFLATGGV LVFLATNVHA                                   570
```

Figure 2

SEQ ID NO. 3

```
  1   SVALTPASGM GLETRAETWM SSEGAWKHAQ RVESWILRNP GFALLAGFMA   50
 51   YMIGQTGIQR TVFFVLMMLV APSYGMRCVG VGNRDFVEGV SGGAWVDLVL  100
101   ENGGCVTTMA QGKPTLDFEL TKTTAKEVAL LRTYCIEASI SNITTATRCP  150
151   TQGEPYLKEE QDQQYICRRD VVDRGWGNGC GLFGKGGVVT CAKFSCSGKI  200
201   TGNLVQIENL EYTVVVTVHN GDTNAVGNDT SNHGVTAMIT PRSPSVEVKL  250
251   PDYGELTLDC FPLSGIDFNE MILMKMKKKT WLVNKQWFLD LPLPWTAGAD  300
301   TSEVHWNYKE RMVTFKSPHA KRQDVTVLGS QEGAMASALA GATEVDSGDG  350
351   NHMFAGALKC KVRMEKLRIK GMSYTMCSGK FSIDKEMAET QAGTTVVQVK  400
401   YEGAGAPCKV PIEIRDVNKE KVVGRIISST PLAENTNSVT NIELEPPFGD  450
451   SYIVIGVGNS ALTLHWFRKG STLGKAFSTT LKGAQRLAAL GDTAWDFGSI  500
501   GGVFNSIGKA VHQVFGGAFR TLFGGMSWIT QGLMGALLLW MGVNARDRSI  550
551   ALAFLATGGV LVFLATNVHA                                   570
```

Figure 3

SEQ ID NO. 4

```
  1   SVALAPAVGM GLDTRTQTWM SAEGAWRQVE KVETWALRHP GFTILALFLA   50
 51   HYIGTSLTQK VVIFILLMLV TPSMTMRCVG VGNRDFVEGL SGATWVDVVL  100
101   ENGGCVTTMA KNKPTLDIEL QKTEATQLAT LRKLCIEGKI TNITTDSRCP  150
151   TQGEAALPEE QDQNYVCKHT YVDRGWGNGC GLFGKGSLVT CAKFQCLEPI  200
201   EGKVVQYENL KYTVIITVHT GDQNQVGNET QGVTVEITPQ ASTTEAILPE  250
251   YGTLGLECFP LTGLDFNEMI LLTMKNKAWM VNRQWFFDLP LPWTSGATTE  300
301   TPTWNRKELL VTFKSAHAKK QEVVVLGSQE GAMATALTGA TEIQNSGGTS  350
351   IFAGALKCRL KMDKLELKGM SYAMCTNTFV LKKEVSETQA GTILIQVEYK  400
401   GEDVPCKIPF STEDGQGKAH NGRLITANPV VTKKEEPVNI EAEPPFGESN  450
451   IVIGIGDNAL KINWYKKGST LGKAFSTTLK GAQRLAALGD TAWDFGSIGG  500
501   VFNSIGKAVH QVFGGAFRTL FGGMSWITQG LMGALLLWMG VNARDRSIAL  550
551   AFLATGGVLV FLATNVHA                                     568
```

Figure 4

SEQ ID NO. 5

1 AGC GTG GCT CTG GCT CCT GCT GTG GGT CTG GGT CTG GAG ACC CGC ACC GAG ACC TGG ATG TCC TCC GAG GGT GCT 75
76 TGG AAG CAG ATC CAG CGC GTG GAG ACC TGG GCT CTG CGC CAC CCT GGT TTC ACC GTG ATC GCT CTG TTC CTG GCT 150
151 CAC GCT ATC GGA ACC TCC ATC ACC CAG AAG GGT ATC ATC TTC ATC CTG CTG ATG CTG GTG ACC CCT TCC ATG GCT 225
226 ATG CGC TGC GTG GGT ATC GGT TCC CGC GAC TTC GTG GAG GGT CTG TCC GGT GCT ACC TGG GTG GAC GTG GTG CTG 300
301 GAG AAC GGT TCC TGC GTG ACC ACC ATG GCT AAG GAC AAG CCT ACC CTG GAC ATC GAG CTG CTG AAG ACC GAG GTG 375
376 ACC AAC CCT GCT GTG CTG CGC AAG CTG TGC ATC GAG GCT AAG ATC TCC AAC ACC ACC ACC GAC TCC CGC TGC CCT 450
451 ACC CAG GGT GAG GCT ACC CTG GTG GAG GAG CAG GAC GCT AAC TTC GTG TGC CGC CGC ACC TTC GTG GAC CGC GGT 525
526 TGG GGT AAC GGT TGC GGT CTG TTC GGT AAG GGT TCC CTG CTG ACC TGC GCT AAG TTC AAG TGC GTG ACC AAG CTG 600
601 GAG GGT AAG ATC GTG CAG TAC GAG AAC CTG AAG TAC TCC GTG ATC GTG ACC GTG CAC ACC GGT GAC CAG AAC CAG 675
676 GTG GGT AAC GAG TCC ACC GAG CAC GGA ACC ACC GCT ACC ATC ACC CCT CAG GCT CCT ACC ACC GAG ATC CAG CTG 750
751 ACC GAC TAC GGT GCT CTG ACC CTG GAC TGC TTC CCT CTG ACC GGT CTG GAC TTC AAC GAG ATG GTG CTG CTG ACC 825
826 ATG AAG GAG AAG TCC TGG CTG GTG AAC AAG CAG TGG TTC CTG GAC CTG CCT CTG CCT TGG ACC TCC GGT GCT TCC 900
901 ACC TCC CAG GAG ACC TGG AAC CGC CAG GAC CTG CTG GTG ACC TTC AAG ACC GCT CAC GCT AAG AAG CAG GAG GTG 975
976 GTG GTG CTG GGT TCC CAG GAG GGT GCT ATG GCT ACC GCT CTG ACC GGT GCT ACC GAG ATC CAG ACC TCC GGA ACC 1050
1051 ACC ACC ATC TTC GCT GGT CAC CTG AAG TGC CGC CTG AAG ATG GAC AAG CTG ACC CTG AAG GGT ATG TCC TAC GTG 1125
1126 ATG TGC ACC GGT TCC TTC AAG CTG GAG AAG GAG GTG GCT GAG ACC CAG GCT GGA ACC GTG CTG GTG CAG ATC AAG 1200
1201 TAC GAG GGA ACC GAC GCT CCT TGC AAG ATC CCT TTC TCC ACC CAG GAC GAG AAG GGT GTG ACC CAG AAC GGT CGC 1275
1276 CTG ATC ACC GCT AAC CCT ATC GTG ACC GAC AAG GAG AAG CCT GTG AAC ATC GAG GCT GAG CCT CCT TTC GGT GAG 1350
1351 TCC TAC ATC GTG ATC GGT GCT GGT GAG AAG GCT CTG AAG CTG TCC TGG TTC AAG AAG GGT TCC ACC CTG GGT AAG 1425
1426 GCT TTC TCC ACC ACC CTG AAG GGT GCT CAG CGC CTG GCT GCT CTG GGT GAC ACC GCT TGG GAC TTC GGT TCC ATC 1500
1501 GGT GGT GTG TTC AAC TCC ATC GGT AAG GCT GTG CAC CAG GTG TTC GGT GGT GCT TTC CGC ACC CTG TTC GGT GGT 1575
1576 ATG TCC TGG ATC ACC CAG GGT CTG ATG GGT GCT CTG CTG CTG TGG ATG GGT GTG AAC GCT GCC GAC CGC TCC ATC 1650
1651 GCT CTG GCT TTC CTG GCT ACC GGT GGT GTG CTG GTG TTC CTG GCT ACC AAC GTG CAC GCT                     1710

Figure 5

SEQ ID NO. 6

1 TCC GTG GCT CTG GTG CCT GCT GTG GGT ATG GGT CTG GAG ACC CGC ACC GAG ACC TGG ATG TCC TCC GAG GGT GCT 75
76 TGG AAG CAC GCT CAG CGC ATC GAG ACC TGG ATC CTG CGC CAC CCT GGT TTC ACC ATC ATG GCT GCT ATC CTG GCT 150
151 TAC ACC ATC GGA ACC ACC CAC TTC CAG CGC GTG CTG ATC TTC ATC CTG CTG ACC GCT GTG GCT CCT TCC ATG ACC 225
226 ATG CGC TGC ATC GGT ATC TCC AAC CGC GAC TTC GTG GAG GGT GTG TCC GGT GGT TCC TGG GTG GAC ATC GTG CTG 300
301 GAG AAC GGT TCC TGC GTG ACC ACC ATG GCT AAG AAC AAG CCT ACC CTG GAC TTC GAG CTG ATC AAG ACC GAG GCT 375
376 AAG CAG CCT GCT ACC CTG CGC AAG TAC TGC ATC GAG GCT AAG CTG ACC AAC ACC ACC GAG TCC CGC TGC CCT 450
451 ACC CAG GGT GAG CCT TCC CTG AAG GAG GAG CAG GAC AAG CGC TTC GTG TGC AAG CAC TCC ATG GTG GAC CGC GGT 525
526 TGG GGT AAC GGT TGC GGT CTG TTC GGT AAG GGT GGT ATC GTG ACC TGC GCT ATG TTC ACC TGC AAG AAG AAC ATG 600
601 GAG GGT AAG ATC GTG CAG CCT GAG AAC CTG GAG TAC ACC ATC GTG GTG ACC CCT CAC TCC GGT GAG GAG AAC GCT 675
676 GTG GGT AAC GAC ACC GGT AAG CAC GGT AAG GAG ATC AAG GTG ACC CCT CAG TCC TCC ATC ACC GAG GCT GAG CTG 750
751 ACC GGT TAC GGA ACC GTG ACC ATG GAG TGC TTC CCT CTG ACC GGT CTG GAC TTC AAC GAG ATG GTG CTG CTG CAG 825
826 ATG GAG AAC AAG GCT TGG CTG GTG AAC CGC CAG TGG TTC CTG GAC CTG CCT CTG CCT TGG CTG CCT GGT GCT GAC 900
901 AAG CAG GAG TCC AAC TGG ATC CAG AAG GAG ACC CTG GTG ACC TTC AAG TCC CCT CAC GCT AAG AAG CAG GAC GTG 975
976 GTG GTG CTG GGT TCC CAG GAG GGT GCT ATG GCT ACC GCT CTG ACC GGT GCT ACC GAG ATC CAG ATG TCC TCC GGT 1050
1051 AAC CTG CTG TTC ACC GGT GCC CTG AAG TGC CGC CTG CGC ATG GAC AAG CTG CAG CTG AAG GGT ATG TCC TAC TCC 1125
1126 ATG TGC ACC GGT AAG TTC AAG GTG GTG AAG GAG ATC GCT GAG ACC CAG GCT GGA ACC ATC GTG ATC AGT GTG CAG 1200
1201 TAC GAG GGT GAC GGT TCC CCT TGC AAG ATC CCT TTC GAG ATC ATG GAC CTG GAG AAG CGC TAC GTG CTG GGT CGC 1275
1276 CTG ATC ACC GTG AAC CCT ATC GTG ACC GAG AAG GAC TCC CCT GTG AAC ATC GAG GCT GAG CCT CCT TTC GGT GAC 1350
1351 TCC TAC ATC ATC ATC GGT GTG GAG CCT GGT CAG CTG AAG CTG AAC TGG TTC AAG AAG GGT TCC ACC CTG GGT AAG 1425
1426 GCT TTC TCC ACC ACC CTG AAG GGT GCT CAG CGC CTG GCT GCT CTG GGT GAC ACC GCT TGG GAC TTC GGT TCC ATC 1500
1501 GGT GGT GTG TTC AAC TCC ATC GGT AAG GCT GTG CAC CAG GTG TTC GGT GGT GCT TTC CGC ACC CTG TTC GGT GGT 1575
1576 ATG TCC TGG ATC ACC CAG GGT CTG ATG GGT GCT CTG CTG CTG TGG ATG GGT GTG AAC GCT CGC GAC CGC TCC ATC 1650
1651 GCT CTG GCT TTC CTG GCT ACC GGT GGT GTG CTG GTG TTC CTG GCT ACC AAC GTG CAC GCT 1710

Figure 6

SEQ ID NO. 7

```
   1 AGC GTG GCT CTG ACC CCT GCT TCC GGT ATG GGT CTG GAG ACC CGC GCT GAG ACC TGG ATG TCC TCC GAG GGT GCT   75
  76 TGG AAG CAC GCT CAG CGC GTG GAG TCC TGG ATC CTG CGC AAC CCT GGT TTC GCT CTG CTG GCT GGT TTC ATG GCT  150
 151 TAC ATG ATC GGT CAG ACC GGT ATC CAG CGC ACC GTG TTC TTC GTG CTG ATG ATG CTG GTG GCT CCT TCC TAC GGT  225
 226 ATG CGC TGC GTG GGT GTG GGT AAC CGC GAC TTC GTG GAG GGT GTG TCC GGT GGT GCT TGG GTG GAC CTG GTG CTG  300
 301 GAG AAC GGT GGT TGC GTG ACC ACC ATG GCT CAG GGT AAG CCT ACC CTG GAC TTC GAG CTG ACC AAG ACC ACC GCT  375
 376 AAG GAG GTG GCT CTG CTG CGC ACC TAC TGC ATC GAG GCT TCC ATC TCC AAC ATC ACC ACC GCT ACC CGC TGC CCT  450
 451 ACC CAG GGT GAG CCT TAC CTG AAG GAG GAG CAG GAC CAG CAG TAC ATC TGC CGC CGC GAC GTG GTG GAC CGC GGT  525
 526 TGG GGT AAC GGT TGC GGT CTG TTC GGT AAG GGT GGT GTG GTG ACC TGC GCT AAG TTC TCC TGC TCC GGT AAG ATC  600
 601 ACC GGT AAC CTG GTG CAG ATC GAG AAC CTG GAG TAC ACC GTG GTG GTG ACC GTG CAC AAC GGT GAC ACC AAC GCT  675
 676 GTG GGT AAC GAC ACC TCC AAC CAC GGT GTG ACC GCT ATG ATC ACC CCT CGC TCC CCT TCC GTG GAG GTG AAG CTG  750
 751 CCT GAC TAC GGT GAG CTG ACC CTG GAC TGC TTC CCT CTG TCC GGT ATC GAC TTC AAC GAG ATG ATC CTG ATG AAG  825
 826 ATG AAG AAG AAG ACC TGG CTG GTG AAC AAG CAG TGG TTC CTG GAC CTG CCT CTG CCT TGG ACC GCT GGT GCT GAC  900
 901 ACC TCC GAG GTG CAC TGG AAC TAC AAG GAG CGC ATG GTG ACC TTC AAG TCC CCT CAC GCT AAG CGC CAG GAC GTG  975
 976 ACC GTG CTG GGT TCC CAG GAG GGT GCT ATG GCT TCC GCT CTG GCT GGT GCT ACC GAG GTG GAC TCC GGT GAC GGT 1050
1051 AAC CAC ATG TTC GCT GGT GCT CTG AAG TGC AAG GTG CGC ATG GAG AAG CTG CGC ATC AAG GGT ATG TCC TAC ACC 1125
1126 ATG TGC TCC GGT AAG TTC TCC ATC GAC AAG GAG ATG GCT GAG ACC CAG GCT GGT ACT ACC GTG GTG CAG GTG AAG 1200
1201 TAC GAG GGT GCT GGT GCT CCT TGC AAG GTG CCT ATC GAG ATC CGC GAC GTG AAC AAG GAG AAG GTG GTG GGT CGC 1275
1276 ATC ATC TCC TCC ACC CCT CTG GCT GAG AAC ACC AAC TCC GTG ACC AAC ATC GAG CTG GAG CCT CCT TTC GGT GAC 1350
1351 TCC TAC ATC GTG ATC GGT GTG GGT AAC TCC GCT CTG ACC CTG CAC TGG TTC CGC AAG GGT TCC ACC CTG GGT AAG 1425
1426 GCC TTC TCC ACC ACC CTG AAG GGT GCT CAG CGC CTG GCT GCT CTG GGT GAC ACC GCT TGG GAC TTC GGT TCC ATC 1500
1501 GGT GGT GTG TTC AAC TCC ATC GGT AAG GCT GTG CAC CAG GTG TTC GGT GGT GCT TTC CGC ACC CTG TTC GGT GGT 1575
1576 ATG TCC TGG ATC ACC CAG GGT CTG ATG GGT GCT CTG CTG CTG TGG ATG GGT GTG AAC GCT CGC GAC CGC TCC ATC 1650
1651 GCT CTG GCT TTC CTG GCT ACC GGT GGT GTG CTG GTG TTC CTG GCT ACC AAC GTG CAC GCT                     1710
```

Figure 7

SEQ ID NO. 8

1 TCC GTG GCT CTG GCT CCT GCT GTG GGT ATG GGT CTG GAC ACC CGC ACC CAG ACC TGG ATG TCC GCT GAG GGT GCT 75
76 TGG CGT CAG GTG GAG AAG GTG GAG ACC TGG GCT CTG CGC CAC CCT GGT TTC ACC ATC CTG GCT CTG TTC CTG GCT 150
151 CAC TAC ATC GGC ACC TCC CTG ACC CAG AAG GTG GTG ATC TTC ATC CTG CTG ATG CTG GTG ACC CCT TCC ATG ACC 225
226 ATG CGC TGC GTG GGT GTG GGT AAC CGC GAC TTC GTG GAG GGT CTG TCC GGT GCT ACC TGG GTG GAC GTG GTG CTG 300
301 GAG AAC GGT GGT TGC GTG ACC ACC ATG GCT AAG AAC AAG CCT ACC CTG GAC ATC GAG CTG CAG AAG ACC GAG GCT 375
376 ACC CAG CTG GCT ACC CTG CGC AAG CTG TGC ATC GAG GGT AAG ATC ACC AAC ATC ACC ACC GAC TCC CGC TGC CCT 450
451 ACC CAG GGT GAG GCT GCT CTG CCT GAG GAG CAG GAC CAG AAC TAC GTG TGC AAG CAC ACC TAC GTG GAC CGC GGT 525
526 TGG GGT AAC GGT TGC GGT CTG TTC GGT AAG GGT TCC CTG GTG ACC TGC GCT AAG TTC CAG TGC CTG GAG CCT ATC 600
601 GAG GGT AAG GTG GTG CAG TAC GAG AAC CTG AAG TAC ACC GTG ATC ATC ACC GTG CAC ACC GGT GAC CAG AAC CAG 675
676 GTG GGT AAC GAG ACC CAG GGT GTG ACC GTG GAG ATC ACC CCT CAG GCT TCC ACC ACC GAG GCT ATC CTG CCT GAG 750
751 TAC GGC ACC CTG GGT CTG GAG TGC TTC CCT CTG ACC GGT CTG GAC TTC AAC GAG ATG ATC CTG CTG ACC ATG AAG 825
826 AAC AAG GCT TGG ATG GTG AAC CGC CAG TGG TTC TTC GAC CTG CCT CTG CCT TGG ACC TCC GGT GCT ACC ACC GAG 900
901 ACC CCT ACC TGG AAC CGC AAG GAG CTG CTG GTG ACC TTC AAG TCC GCT CAC GCT AAG AAG CAG GAG GTG GTG GTG 975
976 CTG GGT TCC CAG GAG GGT GCT ATG GCT ACC GCT CTG ACC GGT GCT ACC GAG ATC CAG AAC TCC GGT GGC ACC TCC 1050
1051 ATC TTC GCT GGT GCT CTG AAG TGC CGC CTG AAG ATG GAC AAG CTG GAG CTG AAG GGT ATG TCC TAC GCT ATG TGC 1125
1126 ACC AAC ACC TTC GTG CTG AAG AAG GAG GTG TCC GAG ACC CAG GCT GGC ACC ATC CTG ATC CAG GTG GAG TAC AAG 1200
1201 GGT GAG GAC GTG CCT TGC AAG ATC CCT TTC TCC ACC GAG GAC GGT CAG GGT AAG GCT CAC AAC GGT CGC CTG ATC 1275
1276 ACC GCT AAC CCT GTG GTG ACC AAG AAG GAG GAG CCT GTG AAC ATC GAG GCT GAG CCT CCT TTC GGT GAG TCC AAC 1350
1351 ATC GTG ATC GGT ATC GGT GAC AAC GCT CTG AAG ATC AAC TGG TAC AAG AAG GGT TCC ACC CTG GGT AAG GCC TTC 1425
1426 TCC ACC ACC CTG AAG GGT GCT CAG CGC CTG GCT GCT CTG GGT GAC ACC GCT TGG GAC TTC GGT TCC ATC GGT GGT 1500
1501 GTG TTC AAC TCC ATC GGT AAG GCT GTG CAC CAG GTG TTC GGT GGT GCT TTC CGC ACC CTG TTC GGT GGT ATG TCC 1575
1576 TGG ATC ACC CAG GGT CTG ATG GGT GCT CTG CTG CTG TGG ATG GGT GTG AAC GCT CGC GAC CGC TCC ATC GCT CTG 1650
1651 GCT TTC CTG GCT ACC GGT GGT GTG CTG GTG TTC CTG GCT ACC AAC GTG CAC GCT TAA                         1704

Figure 8

MATURE VIRUS-LIKE PARTICLES OF FLAVIVIRUSES

RELATED APPLICATIONS

This application is a national stage application, filed under 35 U.S.C. § 371, of International Application No. PCT/TH2019/000015, filed May 28, 2019, which is incorporated herein by reference.

SEQUENCE LISTING

The instant application contains a Sequence Listing which has been submitted electronically in ASCII format and is hereby incorporated by reference in its entirety. The ASCII copy, created on May 2, 2024, is named 542.004US1_2.txt and is 49,840 bytes in size.

TECHNICAL FIELD

The present disclosure relates to virus-like particles (VLPs) or virus structural proteins of flaviviruses incorporated with one or more modified forms that expression of which in the transfected cells results in desired outcome. The VLPs disclosed in several embodiments are preferably fully mature VLPs of flaviviruses. More importantly, the expressed VLPs is capable of eliciting immune response in a mammal such as human subject upon administrating pharmaceutically effective dosage of the expressed VLPs to the mammal. The present disclosure also includes a pharmaceutical or vaccine composition containing the expressed VLPs with or without further modifications applicable for inducing active immunity in a subject against flavivirus.

BACKGROUND

Flavivirus comprise more than 70 different viruses, many of which are arthropod-borne and transmitted by either mosquitoes or ticks. Flavivirus is a genus of viruses in the family Flaviviridae. This genus includes the West Nile virus (WNV), dengue virus (DENV), Japanese encephalitis (JEV), yellow fever virus (YFV), Zika virus (ZikV), tick-borne encephalitis virus (TBEV) and several other viruses which may cause encephalitis or haemorrhagic diseases. Dengue fever is a mosquito-borne disease caused by the dengue virus and has spread to most tropical and many subtropical areas. The disease is caused by four closely related viruses, the Dengue virus type 1 (DENV-1), Dengue virus type 2 (DENV-2), Dengue virus type 3 (DENV-3) and Dengue virus type 4 (DENV-4). Although Dengue virus is the most important flavivirus with respect to global disease incidence, the development and use of vaccines against the virus has been hampered so far by the theoretical risk of vaccine-related adverse events such as immune enhancement of infection and the requirement to induce a long-lasting protective immune response against all four dengue serotypes simultaneously.

Despite intensive research and development efforts to find an effective dengue vaccine in the past decades, there is no reliable vaccine that can prevent dengue following infection by all four serotypes of dengue virus. Recent phase IIb-III trials of Sanofi Pasteur's Dengvaxia in Asia and Latin America revealed a moderately effective vaccine that is unable to provide protection against diseases caused by DENV-2 and in seronegative volunteers (Sabcharoen et al, 2012; Capeding et al, 2014; Villar et al, 2014; Hadinegoro et al, 2015). There is an urgent need to find an alternative dengue vaccine candidate that will be effective against DENV-2 as well as other serotypes, and safe for use in young and seronegative children. Dengue virus-like particles are a potential vaccine candidate that is generated by expressing the two viral envelope glycoproteins, prM and E, in insect or mammalian cells. These two glycoproteins are synthesized as a polyprotein, which is cleaved at specific sites by host proteases; they then associate and assemble into virus-like particles with structural similarities to native virus particles although the virus-like particles do not contain internal core structure or viral genome (Shang et al, 2012). Subsequently, virus-like particles undergo post-translational modifications in the secretory pathway as they are exported out of host cells in the same manner as virus particles in dengue virus-infected cells. As the generation of dengue virus-like particles is not dependent on active virus infection and intracellular replication of the viral genome, the prM and E genes employed in the expression cassette can be modified in a number of ways to enhance export, extracellular level and immunogenicity with lesser constraints than in the modifications of infectious virus particles. Recent understandings on the structures of viral envelope proteins, intracellular and extracellular viral particle subpopulations, the antigenic composition of different types of viral particle, and the antibody responses to envelope proteins in dengue virus-infected persons are crucial to the manipulations aiming at improving dengue virus-like particles' potential as dengue vaccine.

It is well known that extracellular dengue virus particles are a mixture of particles with different maturation levels (Junjhon et al, 2010). Newly assembled, immature viral particles in the ER lumen contain equal quantities of the two envelope glycoproteins, prM and E, which associate as spikes comprising three pairs of non-covalently-linked prM-E heterodimers on the surface of particles (Zhang et al, 2003; Li e al, 2008). During export of particles through the secretory pathway, low pH environment of the Golgi apparatus induces conformational changes of the prM and E proteins (Yu et al, 2008; Zheng et al, 2014), resulting in the dissociation of prM-E dimer and rearrangement of E to form E homodimeric molecules, and allowing cleavage of prM by an endoprotease enzyme, furin (Kuhn et al, 2002; Yu et al, 2008). Cleavage of prM at the pr-M junction generates a 99-residue pr peptide that non-covalently associates with the E dimer under the low pH condition, and the membrane-associated M protein, which interact non-covalently with the underside of the E dimer in mature particles (Zhang et al, 2013). Upon release of particles, the pr peptide dissociates from extracellular particles, generating mature particles with smooth surface and increased infectivity. The presence of a cleavage-inhibitory acidic amino acid residue, glutamic acid or aspartic acid, within the furin recognition site at the pr-M cleavage junction causes incomplete cleavage of prM, resulting in a mixed population of immature, partially mature as well as fully mature, M-containing particles in the extracellular compartment (Junjhon et al, 2008; 2010). Partially mature particles contain patches of E dimers co-existing with those of prM-E heterodimers (Plevka et al, 2011; 2014). The prM-containing immature and partially mature viral particles are less infectious than mature viral particles, but their infectivity against FcRγ+ leukocytes can be enhanced in vitro by either anti-E antibodies or anti-prM antibodies at appropriate concentrations (Rodenhuis-Zybert et al, 2010; Richter et al, 2014).

Differences in the arrangement of prM/M and E in immature vs. mature particles are associated with changes in antigenicity. The E protein in immature particles (and the immature patch of partially mature particles) associates with prM in such a way that certain parts of the E molecule, such as the receptor-binding EDIII domain (Zhang et al, 2003), may not be readily accessible. Upon maturation, dissociation of E from prM and subsequent formation of E homodimer on immature particles (and the mature patch of partially mature particles) result in new epitopes that are formed by adjoining domains of two E molecules in the same dimer as well as between two or more E molecules in different dimers. Epitopes that are dependent on the quaternary structure of E dimers are targets of antibodies that strongly neutralize mature particles (Lok, 2016). In particular, the recently described E dimer-dependent epitopes, which are well conserved between serotypes of dengue virus (Dejniratisai et al, 2015; Rouvinski et al, 2015), can induce cross-reactive neutralizing antibodies that may be useful in the prevention of dengue in areas where several serotypes of dengue virus co-circulate. On the other hand, discrete epitopes found on the monomeric E protein, the form that associates with prM, tends to be hidden on mature particles, resulting in lower target availability that may reduce the activity of these antibodies in the neutralization of mature viral particles (Lok, 2016). A lack of quaternary structure-dependent epitopes on dengue virus-like particles that are not fully mature makes these particles potentially less useful as a vaccine candidate. A comparison of the immunogenicity of VLP generated without or with extensive (83%) prM cleavage showed greater ability of virus-like particles with high level of maturation to induce virus infectivity-neutralizing antibodies in the absence of adjuvant in mice (Suphatrakul et al, 2015).

Furthermore, dengue virus-like particles were generated by co-expressing the two envelope glycoproteins, prM and E, employing native viral nucleic acid sequence (Shang et al, 2012). Dengue virus-like particles generated with using native prM sequence retain some amount of prM (Purdy and Chang, 2005; Konishi and Fujii, 2002; Urakami et al, 2017), which is associated with E in prM-E heterodimers found on the surface of immature and partially mature particles. In certain designs of dengue virus-like particles, the pr-M junction sequence had been modified to abolish prM cleavage by furin (Konishi et al, 2001; Konishi and Fujii, 2002; Yamaji, 2014), resulting in the generation of fully immature virus-like particles. Immature and partially mature virus-like particles, which are generated with native prM sequence or with prM cleavage-abolishing mutations, are capable of inducing prM-specific antibodies. Unlike E-specific antibodies, anti-prM antibodies generally do not neutralize virus infectivity and are unlikely to contribute to protection against dengue. On the other hand, anti-prM antibodies can facilitate infection of FcγR-bearing leukocytes by multiple serotypes of dengue virus (Dejniratisai et al, 2010; Smith et al, 2016) and may contribute to severe disease (Katzelnick et al, 2017). A lack of prM in dengue vaccine candidate is desirable (Dejniratisai et al, 2010; Flipse and Smit, 2015), but is difficult to achieve in the generation of particle-based vaccine candidate (i.e. by deleting the whole prM coding sequence from the prM+E expression cassette) because prM also serves as a chaperone for E protein in its folding in the endoplasmic reticulum (Konishi and Mason, 1993; Lorenz et al, 2002). In the absence of prM, an expression of E protein does not result in the release of membrane-associated particles (Konishi and Mason, 1993; Allison et al, 1995; Hsieh et al, 2014). Our previous attempt to reduce the amount of prM remaining on the extracellular dengue virus-like particles by substituting the acidic amino acid at the pr-M junction with an uncharged residue, such as alanine (Junjhon et al, 2008), in the (prM+E)-expressing vector results in an enhanced, but still incomplete, prM cleavage and the resultant particles can elicit anti-prM antibody response, albeit at reduced level (Suphatrakul et al, 2015). Although this previous design reduces a problem of anti-dengue prM antibody induction, there remains a limitation as quaternary structure-dependent epitopes (within and between E dimers) could not be formed fully in the remaining immature and partially mature particles.

In this design of dengue virus-like particles, the pr-less (M+E)-expressing vector is constructed for the generation of fully mature type of virus-like particles, which, as in the case of extracellular mature viral particles (Kuhn et al, 2002), are devoid of the external pr portion of prM. This modification maximizes the formation of quaternary structure-dependent epitopes on the particles as all E molecules are likely to engage in E homodimer formation. The presence of M allows for an interaction with E as in the mature viral particles (Zhang et al, 2013). As the pr portion of prM contains discrete epitopes in which all known anti-prM monoclonal antibodies and natural anti-prM antibodies from dengue virus-infected persons and immunized animals have been mapped (Chan et al, 2012; Huang et al, 2006, 2008; Luo et al, 2013; Luo et al, 2015; Song et al, 2013; Smith et al, 2016; Wang et al, 2013), a lack of the pr portion of dengue virus prM in this design is also intended to prevent induction of anti-prM antibody response when this virus-like particle is employed as a vaccine in human. Deletion of the pr portion of prM, however, has an undesirable consequence that could affect yield. It is known that one function of prM, particularly the pr portion, is to suppress the fusion of virus particles with intracellular membrane during export (Zheng et al, 2010; Zheng et al, 2014). It is likely that, in the intended absence of the pr portion of prM, the mature virus-like particles could fuse with host cell membrane when they encounter the Golgi apparatus' low pH environment. To minimize acid-induced fusion of mature virus-like particles with Golgi apparatus membrane during export, a number of conserved and internally-located histidine residues in the M and E proteins, including histidine residues at positions 7, 102, 224, 284 (282 for DENV-3), 336 (334 for DENV-3), 357 (355 for DENV-3) and 392 (390 for DENV-3), are substituted with alanine or asparagine. This is based on previous findings that histidine serves as pH sensor, and protonation of histidine in the acidic environment leads to conformational changes of E and prM both during export (resulting in the conversion from prM-E heterodimer to E dimer) and during fusion with endosomal membrane in new virus-infected cells (resulting in the conversion from E dimer to E trimer) (Kampmann et al, 2006; Mueller et al, 2008; Fritz et al, 2008; Fuzo and Degrève, 2014; Zheng et al, 2014; Chaudhury et al, 2015). In this application, multiple histidine residues are substituted concurrently as single substitution of any histidine residue is unlikely to abrogate fusion (Nelson et al, 2009; Chaudhury et al, 2015) and increase yield (Christian et al, 2013). Histidine residues that can be accessed from the surface are not substituted to preserve the antigenicity of the E protein. Additional modifications of the E protein involve substitutions on the lateral side of the E dimer, including non-histidine residues at the positions 261 (259 for DENV-3), 263 (261 for DENV-3), 317 (315 for DENV-3) and 398 (396 for DENV-3) to increase the release of virus-like particles (Christian et al, 2013), and substitution at the fusion loop of E, including residues at the positions E107 or E108, to reduce the fusion potential of the E protein (Trainor et al, 2007; Christian et al, 2013; Urakami et al, 2017). Nonetheless, the expression of these virus-like particles in the extracellular level is still far from satisfying. Further modification on the dengue virus-like particles, M and E proteins, are therefore needed such that the increased extracellular virus-like particles may result in better or improved immune response in the subject being vaccinated with these virus-like particles.

SUMMARY

The present disclosure, in several embodiments, aims to provide mature flavivirus-like particles that are able to induce or elicit active immune response in a subject after administrating the particles to the subject under appropriate dosage. The mature particles are genetically modified such that the expressed modified particles become more resistant against acid-induced conformational changes or fusion when these expressed particles are transported out of the host cells.

Another object of the present disclosure is to offer a chimeric peptide or virus structural protein comprising a modified form of joined M and E proteins of flavivirus. Preferably, the signal sequence for the M protein and the C-terminal stem-anchor domain of the E protein in the disclosed chimeric peptide are substituted with the corresponding regions from the Defensin A protein of *Aedes aegypti* and the E protein of Japanese encephalitis virus, respectively, to enhance the level of extracellular virus-like particles.

Further object of the present disclosure includes offering a vaccine composition being configured to effectively react against flavivirus infection, or more particularly dengue virus infection, containing the above mentioned modified and/or chimeric peptides. Administrating and exposing a subject with the disclosed vaccine composition having the modified peptides and/or chimeric for a suitable period shall induce active immunization of the exposed subject.

At least one of the preceding objects is met, in whole or in part, by the present disclosure, in which one of the embodiments of the present disclosure relates to a virus-like particle capable of eliciting immune response in a mammal. The virus-like particles or peptides preferably comprise an amino acids sequence substantially corresponding to a sequence setting forth in SEQ ID NO. 1, SEQ ID NO. 2, SEQ ID NO. 3 or SEQ ID NO. 4, which carries one or more human-made or artificial modifications or modified forms of dengue virus sequence. The modifications or modified forms may include conserved amino acid His at positions M7, E261, E282, and E317 of dengue virus sequence, which are replaced by amino acid Ala at positions 7, 336, 357 and 392 in SEQ ID NO. 1-3, or conserved amino acid His at positions M7, E259, E280 and E315 of dengue virus sequence are replaced by amino acid Ala at positions 7, 334, 355 and 390 in SEQ ID NO. 4. It is crucial to note that the disclosed VLPs are being subjected to modifications or modified forms involving combining the dengue virus M protein (free from the pr peptide) with the E protein at specific positions for acquiring better expression at the extracellular level.

In some other embodiments, the modified forms further comprise replacement of conserved amino acid His at positions E27, E149 and E209 of dengue virus sequence with amino acid Asn at positions 102, 224 and 284 in SEQ ID NO. 1-3 or replacement of conserved amino acid His at positions E27, E149 and E207 of dengue virus sequence with amino acid Asn at positions 102, 224 and 282 in SEQ ID NO. 4.

For other embodiments, the modifications further comprises any one or combination of replacement of amino acids Ser or Glu at position E186 of dengue virus sequence or amino acid Ser at position E184 of dengue virus sequence with amino acid Phe at position 261 in SEQ ID NO. 1-3 or at position 259 in SEQ ID NO. 4, respectively, replacement of amino acid Arg located at position E188 of dengue virus sequence or position E186 of dengue virus sequence with amino acid Leu at position 263 in SEQ ID NO. 1-3 or at position 261 in SEQ ID NO. 4, replacement of amino acid Asn or Val at position E242 of dengue virus sequence or amino acid Asn at position E240 of dengue virus sequence with amino acid Ser at position 317 in SEQ ID NO. 2-3 or position 315 in SEQ ID NO. 4, and replacement of amino acid Arg or Lys located at position E323 of dengue virus sequence or amino acid Lys position E321 of dengue virus sequence with amino acid Gln at position 398 of SEQ ID NO. 2-3 or position 396 of SEQ ID NO. 4.

According to several embodiments, the virus-like particle is of flavivirus origin. More preferably, the flavivirus which the modified peptides or proteins generally derived from is dengue virus, Japanese encephalitis virus, Yellow fever virus, West Nile virus or Zika virus. For instance, in some embodiments, the signal sequence for the M protein and the C-terminal stem-anchor domain of the E protein in the disclosed chimeric peptide are substituted with the corresponding regions from the Defensin A protein of *Aedes aegypti* and the E protein of Japanese encephalitis virus, respectively, to enhance the level of extracellular virus-like particles.

Another aspect of the present disclosure relates to an isolated polynucleotide encoding a virus-like particle or polypeptide capable of eliciting immune response in a subject upon administrating the virus-like particle or polypeptide to the subject at a pharmaceutically effective dosage. More particularly, the virus-like particle or polypeptide comprises a modified form of M and E structural proteins of flavivirus, wherein an amino acids sequence substantially corresponding to a sequence setting forth in SEQ ID NO. 1, SEQ ID NO. 2, SEQ ID NO. 3 or SEQ ID NO. 4, wherein conserved amino acid His at positions M7, E261, E282 and E317 of dengue virus sequence are replaced with amino acid Ala at positions 7, 336, 357, and 392 in SEQ ID NO. 1-3 or conserved amino acid His at positions M7, E259, E280 and E315 of dengue virus sequence are replaced with amino acid Ala at positions 7, 334, 355 and 390 in SEQ ID NO. 4. The alterations or modifications or modified forms shall render better expression of the protein in the extracellular level bringing forth better immunization towards the flavivirus in the subject being vaccinated using the disclosed composition.

To further increase the extracellular level expression, the disclosed particles may further comprise replacement of conserved amino acid His at positions E27, E149 and E209 of dengue virus sequence with amino acid Asn at positions 102, 224 and 284 in SEQ ID NO. 1-3 or replacement of conserved amino acid His at positions E27, E149 and E207 of dengue virus sequence with amino acid Asn at positions 102, 224 and 282 in SEQ ID NO. 4. Also, the modifications or modified forms further comprise any one or combination of replacement of amino acid Ser or Glu at position E186 of dengue virus sequence or amino acid Ser at position E184 of dengue virus sequence with amino acid Phe at position 261 of SEQ ID NO. 1-3 or at position 259 of SEQ ID NO. 4, respectively, replacement of amino acid Arg at position E188 of dengue virus sequence or position E186 of dengue virus sequence with amino acid Leu at position 263 in SEQ ID NO. 1-3, or at position 261 in SEQ ID NO. 4, respectively, replacement of amino acid Asn or Val at position E242 of dengue virus sequence or amino acid Asn at position E240 of dengue virus sequence with amino acid Ser at position 317 in SEQ ID NO. 2-3 or position 315 in SEQ ID NO. 4, and replacement of amino acid Arg or Lys located at position E323 of dengue virus sequence or amino acid Lys position E321 of dengue virus sequence with amino acid Gln at position 398 of SEQ ID NO. 2-3 or position 396 of SEQ ID NO. 4. In addition, the distal part of the E proteins (positions 472-570 of SEQ ID NO. 1-3 or positions 470-568 of SEQ ID NO. 4) is substituted with the corresponding sequence of Japanese encephalitis virus for some embodiments.

Further aspect of the present disclosure is directed to a vaccine composition effective against flavivirus such as dengue virus infection. Particularly, the vaccine composition comprises a pharmaceutically acceptable adjuvant; and modified flavivirus polypeptides or virus-like particles, which are immunologically active upon administrating to a subject. The modified flavivirus polypeptides have an amino acids sequence substantially corresponding to a sequence setting forth in SEQ ID NO. 1, SEQ ID NO. 2, SEQ ID NO. 3 or SEQ ID NO. 4. The amino acids sequence comprises a modified form or modification of dengue virus sequence, wherein conserved amino acid His at positions M7, E261, E282, and E317 of dengue virus sequence, are replaced by amino acid Ala at positions 7, 336, 357 and 392 in SEQ ID NO. 1-3, or conserved amino acid His at positions M7, E259, E280 and E315 of dengue virus sequence are replaced by amino acid Ala at positions 7, 334, 355 and 390 in SEQ ID NO. 4.

For a number of embodiments, the polypeptides in the vaccine composition possess more modified forms or modifications including replacement of conserved amino acid His at positions E27, E149 and E209 of dengue virus sequence with amino acid Asn at positions 102, 224 and 284 in SEQ ID NO. 1-3 or replacement of conserved amino acid His at positions E27, E149 and E207 of dengue virus sequence with amino acid Asn at positions 102, 224 and 282 in SEQ ID NO. 4.

BRIEF DESCRIPTION OF DRAWINGS

FIG. 1 shows the modified amino acid sequence of flavivirus structural proteins (M and E) derived from DENV-1 and Japanese encephalitis virus and identified as SEQ ID NO. 1;

FIG. 2 shows the modified amino acid sequence of flavivirus structural proteins (M and E) derived from DENV-2 and Japanese encephalitis virus and identified as SEQ ID NO. 2;

FIG. 3 shows the modified amino acid sequence of flavivirus structural proteins (M and E) derived from DENV-3 and Japanese encephalitis virus and identified as SEQ ID NO. 4;

FIG. 4 shows the modified amino acid sequence of flavivirus structural proteins (M and E) derived from DENV-4 and Japanese encephalitis virus and identified as SEQ ID NO. 3;

FIG. 5 shows the modified nucleotide sequence encoding the flavivirus structural proteins (M and E) of DENV-1 virus-like particles and identified as SEQ ID NO. 5;

FIG. 6 shows the modified nucleotide sequence encoding the flavivirus structural proteins (M and E) of DENV-2 virus-like particles and identified as SEQ ID NO. 6;

FIG. 7 shows the modified nucleotide sequence encoding the flavivirus structural proteins (M and E) of DENV-4 virus-like particles and identified as SEQ ID NO. 7;

FIG. 8 shows the modified nucleotide sequence encoding the flavivirus structural proteins (M and E) of DENV-3 virus-like particles and identified as SEQ ID NO. 8;

DETAILED DESCRIPTION

Figure 9:
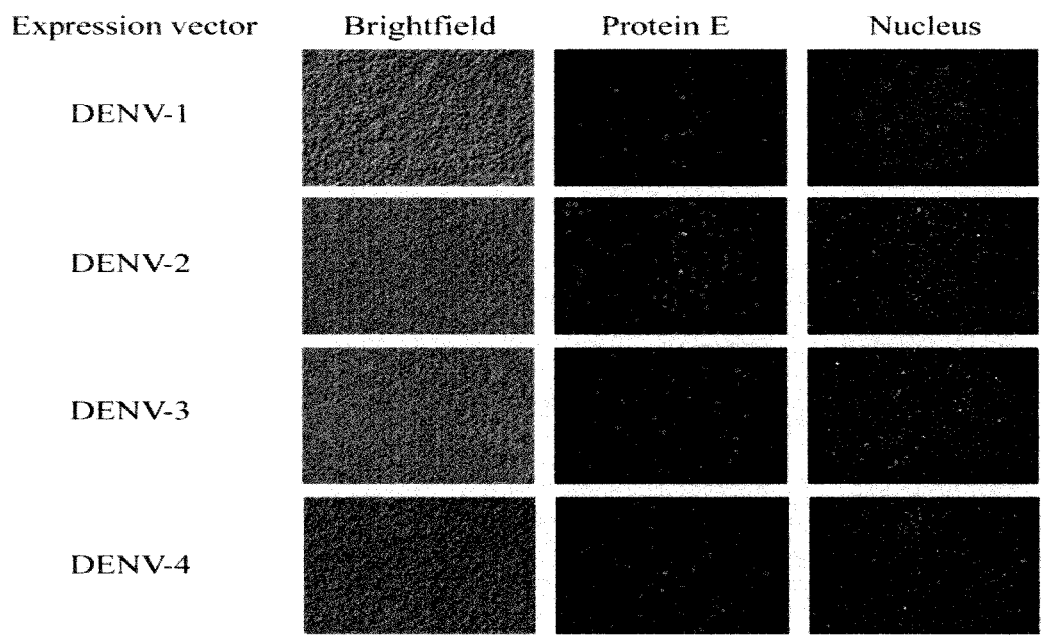
FIG. 9 shows the intracellular expression of the viral protein E following transfection of mosquito cells with the expression vector for the expression of DENV-1, DENV-2, DENV-3, and DENV-4 virus-like particles that the E protein was demonstrated by indirect immunofluorescence assay with a mouse monoclonal anti-E antibody, 1D10, and Cy3-conjugated goat anti-mouse IgG antibody and nuclei were revealed by staining with DAPI.
Figure 10:
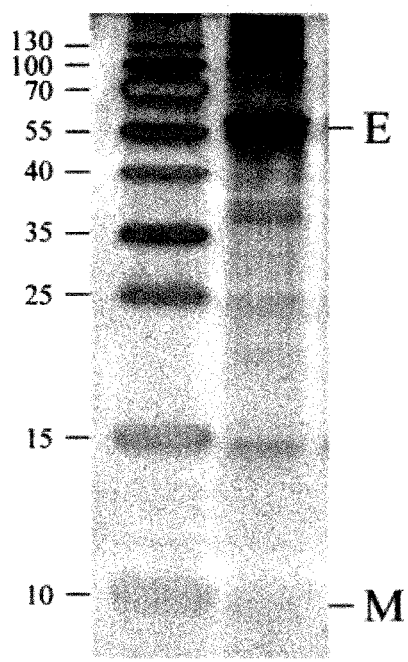
FIG. 10 shows sodium dodecyl sulfate-polyacrylamide gel electrophoresis and silver staining of M and E proteins in fractions derived from purified DENV-1 mature virus-like particles that the virus-like particle was purified by 20%-55% sucrose step gradient centrifugation followed by rate zonal centrifugation, where the size of protein markers is indicated on the left.
Figure 11:
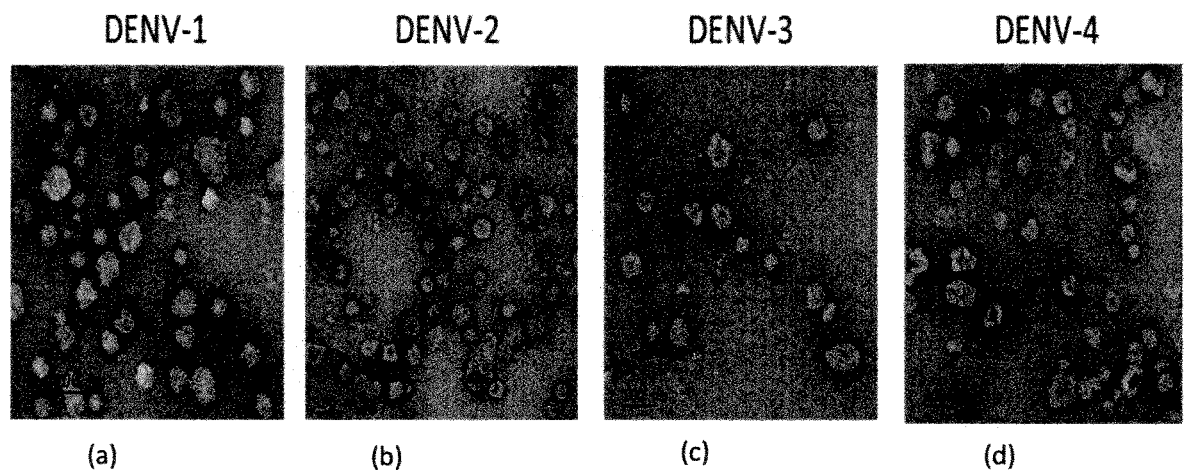
FIG. 11 illustrates transmission electron micrographs of (a) purified DENV-1 virus-like particles, (b) purified DENV-2 virus-like particles, (c) purified DENV-3 virus-like particles and (d) purified DENV-4 virus-like particles.
Figure 12:
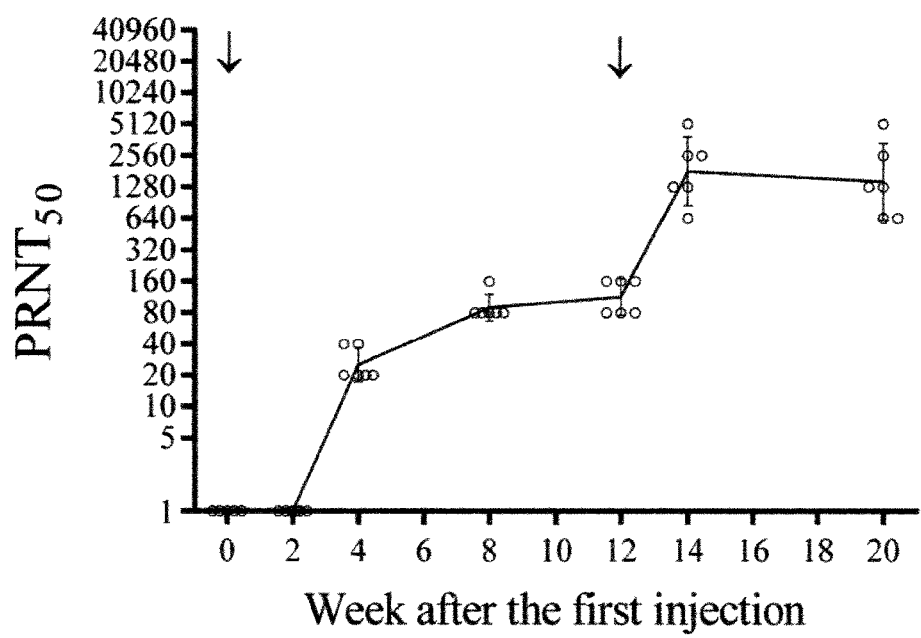
FIG. 12 illustrates the neutralizing antibody response after the injection of DENV-2 virus-like particles in to 6 mice at weeks 0 and 12 that the reciprocal 50% plaque reduction neutralization titers (PRNT50) of mouse sera obtained at different time points (weeks 0, 2, 4, 8, 12, 14 and 20) are plotted with each of the dots represents an individual mouse, where the line connects the geometric mean titer and error bars denote standard deviation.
Figure 13:
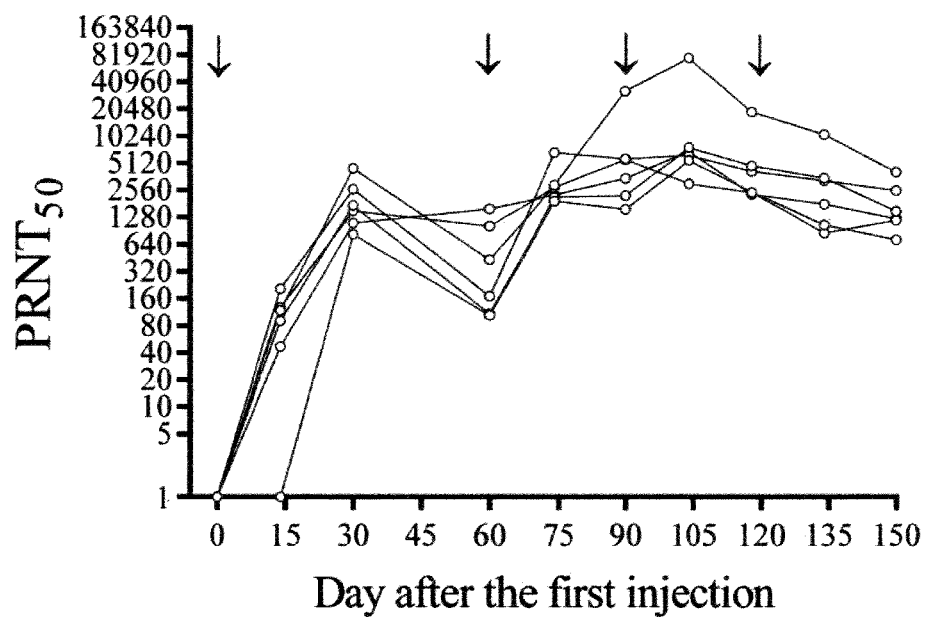
FIG. 13 illustrates the neutralizing antibody response in cynomolgus macaques after the prime-injection of a DENV-2 live attenuated virus on day 0, two booster injections with the DENV-2 virus-like particles on days 60 and 90, and a challenge injection with a DENV-2 wild type virus on day 120, where the reciprocal 50% plaque reduction neutralization titers (PRNT50) of macaque sera obtained at different time points (days 0, 14, 30, 60, 74, 90, 104, 118, 134 and 150) are plotted with each of the dots and connecting line represent individual macaque.

Hereinafter, the disclosure shall be described according to the preferred embodiments and by referring to the accompanying description and drawings. However, it is to be understood that referring the description to the preferred embodiments of the invention and to the drawings is merely to facilitate discussion of the various disclosed embodiments and it is envisioned that those skilled in the art may devise various modifications without departing from the scope of the appended claim.

Unless specified otherwise, the terms "comprising" and "comprise" as used herein, and grammatical variants thereof, are intended to represent "open" or "inclusive" language such that they include recited elements but also permit inclusion of additional, un-recited elements.

As used herein, the phrase "in embodiments" means in some embodiments but not necessarily in all embodiments.

The term "polypeptides" used herein throughout the disclosure refers to a chain of amino acids linked together by peptide bonds but with a lower molecular weight than protein. Polypeptides can be obtained by synthesis or hydrolysis of proteins. Few polypeptides can be joined together by any known method in the art to form a functional unit.

The term "polynucleotide" or "nucleic acid" as used herein designates mRNA, RNA, cRNA, cDNA or DNA. The term typically refers to oligonucleotides greater than 30 nucleotide residues in length.

The terms "partial" or "substantially corresponding to" used herein to describe the polypeptides or peptides throughout the disclosure refers to polypeptides or peptides that contain at least 70%, or more preferably at least 80%, sequential amino acids identical to the disclosed polypeptides or peptides as shown in FIG. 1-4. These polypeptides though may not have the sequence fully identical to disclosed polypeptides or peptides; these polypeptides may retain the active epitopes to react with the corresponding antibodies to elicit the desired immune response against flavivirus and these active epitopes are present on the peptides due to the sequence of the amino acids arranged in the peptides has about at least 70% to 90% similarity to the disclosed sequence by alignment.

As used herein, "a position corresponding to" or recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm. By aligning the sequences, one skilled in the art can identify corresponding residues.

The term "dengue sequence" or "dengue virus sequence" as used herein refers to a linear nucleotide or amino acid sequence or sequences of dengue virus, particularly a wild-type virus or a wild type of dengue virus having nucleotides or amino acids at position(s) corresponding to any known or naturally occurred sequence of dengue virus. In the disclosure, the term "dengue sequence" or "dengue virus sequence" is also used interchangeably.

In the specification and claims of the present disclosure, the term "flavivirus structural protein" or "flavivirus peptide" or "flavivirus polypeptide" are used interchangeably referring to any peptide-based sequence derived from flavivirus that can be recognized by the immune system in a subject, stimulates a cell-mediated immune response in a subject and/or stimulates the generation of antibodies in a subject.

The flavivirus selected in the present disclosure as the template or original structure or peptide-sequence structure for modification into the disclosed peptides or proteins may derive from Dengue virus, Yellow fever virus, Japanese encephalitis virus, West Nile virus and/or Zika virus. For some embodiments, one portion or region of the proteins derived from one virus type may be replaced or substituted by corresponding or similar region of other virus type. For example, the signal sequence for the M protein of Dengue virus origin is removed and substituted with the corresponding regions originated from the Defensin A protein of *Aedes aegypti*. Similar modifications can be seen in other embodiments in which the C-terminal stem-anchor domain of the E protein originated from Dengue virus is replaced with corresponding region of the E protein from Japanese encephalitis virus. Such modifications involve moving or replacing one region of a protein of one virus type to protein of another virus type aims to improve yield of the expressed disclosed peptides or protein at the extracellular level. In accordance with several preferred embodiments, the flavivirus which the disclosed peptides originally or naturally acquired from is Dengue virus. The Dengue virus may be Dengue virus 1 including subtypes I to IV, Dengue virus 2 including subtypes Asian I, Asian II, Cosmopolitan, American and American/Asian, Dengue virus 3 including subtypes I to IV and Dengue virus 4 including subtypes I to III. Generally, Dengue virus structural protein consists of capsid protein, precursor membrane (prM) protein, membrane (M) protein and envelope (E) protein. For more embodiments, the disclosure proteins or peptides are mature virus-like particle comprises two of those structural proteins, namely the M protein and the E protein. The dengue virus structural protein may further comprise an amino acid corresponding to the initiation codon and a signal sequence to the amino terminus of the M sequence.

More specifically, some embodiments of the present disclosure provide a mature virus-like particle comprising a modified form of M and E structural proteins of flavivirus, wherein multiple amino acids are altered from its naturally occurred structure. These structural proteins can be expressed by using any known method in the field through a group of selected host cells or animal. One or more flavivirus structural proteins disclosed may be used for subject immunization as long as they spontaneously assemble into a particulate structure having active epitope for binding with the antibody to initiate the immunization process. For example, when eukaryotic cells expressing a gene encoding M and E proteins of dengue virus are cultured, the proteins are generated by the cells and assemble into virus-like particles and the virus-like particles can be collected from the cell culture media. Alternatively, chemical synthesis method can be employed as well giving rise to the interested structural protein identical or almost identical to the flavivirus structural proteins, M and E. Preferably, the created or expressed proteins of M and E are associated, joined, attached or held in a manner exposing the deliberately retain epitopes to yield the expected immune response in a subject.

The modified forms of M and E region of the flavivirus, or particularly dengue virus, amino acid sequences are represented by SEQ ID NO. 1-4. Viral structural proteins of various flaviviruses such as dengue virus types 1+4 have been identified and available at various public databases such as GenBank database. For example, Dengue virus type 1 (strain West Pac and strain 16007): Accession No. U88535 and AF180817.1, Dengue virus type 2 (strain SI vaccine and strain 16681): Accession No. M19197 and U87411.1, Dengue virus type 3 (strain Singapore 8120/95 and strain 16562): Accession No. AY766104 and KU725665.1 and Dengue virus type 4 (strain ThD4_0476_97 and strain H-241): Accession No. Y618988.1 and U18433.1. The information with respect to envelope protein including sequential amino acids arrangement of a flavivirus such as dengue virus may be obtained from a database. By using the sequence alignment function in these databases, person skilled in the field shall be able to identify substantial length of SEQ ID NO. 1-4 being incorporated into a much longer sequence of a larger peptide or found a partial segment of SEQ ID NO. 1-4 in a shorter sequence of a relatively smaller peptide. Any modifications or modified forms of these longer or shorter sequences closely related to the disclosed SEQ ID NO. 1-4 shall not depart from the scope of the present disclosure as long such modifications lead to better or improved induced immune response in the subject against flavivirus or dengue virus. It is important to note that the peptides expressed through the disclosed sequences are free of the pr portion of prM.

Accordingly, the disclosed peptides of SEQ ID NO. 1-4 are made or produced to include at least one amino acid alternation, preferably between amino acid position 7 and amino acid position 398, or between the positions determined as the above-identified positions when the amino acid sequence of a flavivirus or a fragment thereof is aligned with SEQ ID NO. 1-4. More specifically, the region comprising at least one amino acid alternations or modifications may be preferably between amino acid position 7 and amino acid position 398 of SEQ ID NO. 1-4. Some embodiments of the expressed peptides may commonly comprise initiation codon Met and signalling peptide followed by M and E of Dengue Virus 1, Dengue Virus 2, Dengue Virus 3, or Dengue Virus 4 in some embodiments. The initiation codon, signalling region, peptide M and peptide E are preferably arranged in sequential tandem. For several embodiments, the distal part of the E proteins is substituted or incorporated with the corresponding sequence of Japanese encephalitis virus. The presently disclosed protein, peptides or virus-like particle is capable of eliciting immune response in a mammal or subject comprising an amino acids sequence substantially corresponding to a sequence setting forth in SEQ ID NO. 1, SEQ ID NO. 2, SEQ ID NO. 3 or SEQ ID NO. 4. The disclosed amino sequence carries the desired modifications. For a number of embodiments, the modified form comprises an amino acids sequence substantially corresponding to an M and E sequence setting forth in SEQ ID NO. 1, SEQ ID NO. 2, SEQ ID NO. 3 or SEQ ID NO. 4, wherein conserved amino acid His at positions M7, E261, E282, and E317 of dengue virus sequence, are replaced by amino acid Ala at positions 7, 336, 357 and 392 in SEQ ID NO. 1-3, or conserved amino acid His at positions M7, E259, E280 and E315 of dengue virus sequence are replaced by amino acid Ala at positions 7, 334, 355 and 390 in SEQ ID NO. 4.

In more embodiments, the modified form further comprises replacement of conserved amino acid His at positions E27, E149 and E209 of dengue virus sequence with amino acid Asn at positions 102, 224 and 284 in SEQ ID NO. 1-3 or replacement of conserved amino acid His at positions E27, E149 and E207 of dengue virus sequence with amino acid Asn at positions 102, 224 and 282 in SEQ ID NO. 4. Also, the modified forms or the modifications on the disclosed sequences further comprises any one or combination of replacement of amino acids Ser or Glu at position E186 of dengue virus sequence or amino acid Ser at position E184 of dengue virus sequence with amino acid Phe at position 261 in SEQ ID NO. 1-3 or at position 259 in SEQ ID NO. 4, respectively, or replacement of amino acid Arg at position E188 of dengue virus sequence or position E186 of dengue virus sequence with amino acid Leu at position 263 in SEQ ID NO. 1-3 or at position 261 in SEQ ID NO. 4, respectively, or replacement of amino acid Asn or Val at position E242 of dengue virus sequence or amino acid Asn at position E240 of dengue virus sequence with amino acid Ser at position 317 in SEQ ID NO. 2-3 or position 315 in SEQ ID NO. 4, or replacement of amino acid Arg or Lys located at position E323 of dengue virus sequence or amino acid Lys position E321 of dengue virus sequence with amino acid Gln at position 398 of SEQ ID NO. 2-3 or position 396 of SEQ ID NO. 4.

With the exception of comprising at least one amino acid alteration in the region, a flavivirus structural protein contained in the virus-like particle may be a naturally occurring viral structural protein or a modified protein thereof. In plurality of embodiments, the modified protein has at least 70%, 75%, 80%, 85%, 90%, 95% or 98% amino acid sequence identity to a naturally occurring viral structural protein including M and E proteins. For more embodiments, the modified protein is a mutant with potentially at most 10% of the amino acids corresponding the sequence of SEQ ID NO. 1-4 are deleted, substituted, and/or added to a naturally occurring viral structural protein including M and envelope regions. The sequence identity may be determined by conventional methods.

The modified flavivirus structural protein may have at least 70%, 75%, 80%, 85%, 90%, 95% or 98% amino acid sequence identity to an amino acid sequence represented by any one of SEQ ID Nos. 1-4. Also, the modified flavivirus structural protein may be a mutant where at most 10% of the amino acids are deleted, substituted, and/or added based on the flavivirus structural protein having an amino acid sequence represented by any one of SEQ ID NO. 1-4.

The second aspect of the present disclosure is directed to an isolated polynucleotide or nucleic acid molecule comprising a nucleotide sequence encoding the virus-like particle setting forth in SEQ ID NO. 1-4 with or without modifications. Preferably, the isolated polynucleotide encoding a virus-like particle or polypeptide capable of eliciting immune response in a subject upon administrating the virus-like particle or polypeptide to the subject at a pharmaceutically effective dosage. The virus-like particle, peptide or polypeptide encoded by the disclosed polynucleotide comprises a modified form of M and E structural proteins of flavivirus, wherein a nucleotide sequence of the modified form is substantially corresponding to a sequence setting forth in SEQ ID NO. 5, SEQ ID NO. 6, SEQ ID NO. 7 or SEQ ID NO. 8, or an amino acids sequence substantially corresponding to a sequence setting forth in SEQ ID NO. 1, SEQ ID NO. 2, SEQ ID NO. 3 or SEQ ID NO. 4, wherein conserved amino acid His at positions M7, E261, E282 and E317 of dengue virus sequence are replaced with amino acid Ala at positions 7, 336, 357, and 392 in SEQ ID NO. 1-3 or conserved amino acid His at positions M7, E259, E280 and E315 of dengue virus sequence are replaced with amino acid Ala at positions 7, 334, 355 and 390 in SEQ ID NO. 4.

In accordance with several embodiments of the disclosed nucleic acid molecule, it may encode as well the modifications of replacement of conserved amino acid His located at positions E27, E149 and E209 of dengue virus sequence with amino acid Asn at positions 102, 224 and 284 in SEQ ID NO. 1-3 or replacement of conserved amino acid His at positions E27, E149 and E207 of dengue virus sequence with amino acid Asn at positions 102, 224 and 282 in SEQ ID NO. 4. Similarly, for more embodiments, the modifications encoded in the disclosed nucleic acid molecule further comprises any one or combination of replacement of amino acid Ser or Glu at position E186 of dengue virus sequence or amino acid Ser at position E184 of dengue virus sequence with amino acid Phe at position 261 of SEQ ID NO. 1-3 or at position 259 of SEQ ID NO. 4, respectively, replacement of amino acid Arg at position E188 of dengue virus sequence or position E186 of dengue virus sequence with amino acid Leu at position 263 in SEQ ID NO. 1-3, or at position 261 in SEQ ID NO. 4, respectively, amino acid Asn or Val at position E242 of dengue virus sequence or amino acid Asn at position E240 of dengue virus sequence with amino acid Ser at position 317 in SEQ ID NO. 2-3 or position 315 in SEQ ID NO. 4, and replacement of amino acid Arg or Lys at position E323 of dengue virus sequence or amino acid Lys position E321 of dengue virus sequence with amino acid Gln at position 398 of SEQ ID NO. 2-3 or position 396 of SEQ ID NO. 4.

It is important to note that multiple variants of the polynucleotide can be used for encoding the modified proteins or peptide since a single amino acid can be encoded by more than one nucleotide codon. Representative example of the variants respectively encoding for proteins of SEQ ID NO. 1-4 are respectively illustrated in FIG. 5-8 as SEQ ID NO. 5-8. More importantly, for some embodiments, the present disclosure provides a nucleic acid molecule which is further modified from the nucleic acid molecule having a nucleotide sequence represented by any one of SEQ ID Nos. 5-8. The modified nucleic acid molecule may have at least 70%, 75%, 80%, 85%, 90%, 95% or 98% nucleotide sequence identity to the nucleic acid molecule having a nucleotide sequence represented by any one of SEQ ID Nos. 5-8. Also, the modified nucleic acid molecule may be a mutant where at most 10% of the amino acids are deleted, substituted, and/or added based on the nucleic acid molecule having a nucleotide sequence represented by any one of SEQ ID Nos. 5-8.

Further embodiments of the disclosure contain an expression vector comprising the nucleic acid molecule described above. The vector optionally comprises an expression control sequence operably linked to the disclosed nucleic acid molecule. More specifically, the present disclosure provides an expression vector for flavivirus structural proteins, M and E that the expression vector carries a nucleotide sequence encoding the variants of protein setting forth in SEQ ID NO. 1-4 with the above-mentioned amino acid replacement. The nucleotide sequence carried by the expression vector can be any one of SEQ ID Nos. 5-8.

Third aspect of the present disclosure provides a composition or vaccine composition comprising the virus-like particle provided in the first aspect of the present application and/or the nucleic acid molecule provided in the second aspect of the present invention. Particularly, the vaccine composition comprises pharmaceutically acceptable adjuvant; and polypeptides or virus-like particles, which are immunologically active upon administrating to a subject, having an amino acids sequence substantially corresponding to a sequence setting forth in SEQ ID NO. 1, SEQ ID NO. 2, SEQ ID NO. 3 or SEQ ID NO. 4. Each of the disclosed sequences is incorporated with one or more modified forms or modifications of dengue virus sequence, wherein conserved amino acid His at positions M7, E261, E282, and E317 of dengue virus sequence, are replaced by amino acid Ala at positions 7, 336, 357 and 392 in SEQ ID NO. 1-3, or conserved amino acid His at positions M7, E259, E280 and E315 of dengue virus sequence are replaced by amino acid Ala at positions 7, 334, 355 and 390 in SEQ ID NO. 4.

For more embodiments of the disclosed vaccine composition, the modified forms or modifications further comprise replacement of conserved amino acid His at positions E27, E149 and E209 of dengue virus sequence with amino acid Asn at positions 102, 224 and 284 in SEQ ID NO. 1-3 or replacement of conserved amino acid His at positions E27, E149 and E207 of dengue virus sequence with amino acid Asn at positions 102, 224 and 282 in SEQ ID NO. 4.

In several more embodiments of the disclosed vaccine composition, the modified forms or modifications further comprise any one or combination of replacement of amino acids Ser or Glu at position E186 of dengue virus sequence or amino acid Ser at position E184 of dengue virus sequence with amino acid Phe at position 261 in SEQ ID NO. 1-3 or at position 259 in SEQ ID NO. 4, respectively, replacement of amino acid Arg located at position E188 of dengue virus sequence or position E186 of dengue virus sequence with amino acid Leu at position 263 in SEQ ID NO. 1-3 or at position 261 in SEQ ID NO. 4, replacement of amino acid Asn or Val at position E242 of dengue virus sequence or amino acid Asn at position E240 of dengue virus sequence with amino acid Ser at position 317 in SEQ ID NO. 2-3 or position 315 in SEQ ID NO. 4, and replacement of amino acid Arg or Lys located at position E323 of dengue virus sequence or amino acid Lys position E321 of dengue virus sequence with amino acid Gln at position 398 of SEQ ID NO. 2-3 or position 396 of SEQ ID NO. 4.

In some embodiments, the modified forms of both the M and E structural proteins comprise one or more amino acid substitution of SEQ ID NO: 9, wherein SEQ ID NO: 9 comprises amino acids 206-676 of dengue virus type 1 polyprotein (strain West Pac) (Genbank Accession No. U88535) and amino acids 695-794 of Japanese encephalitis (strain Nakayama; Genbank Accession No. EF571853.1) E structural protein.

(SEQ ID NO: 9)
SVALAPHVGLGLETRTETWMSSEGAWKQIQKVETWALRHPGFTVIALFL

AHAIGTSITQKGIIFILLMLVTPSMAMRCVGIGNRDFVEGLSGATWVDV

VLEHGSCVTTMAKDKPTLDIELLKTEVTNPAVLRKLCIEAKISNTTTDS

RCPTQGEATLVEEQDTNFVCRRTFVDRGWGNGCGLFGKGSLITCAKFKC

VTKLEGKIVQYENLKYSVIVTVHTGDQHQVGNETTEHGTTATITPQAPT

SEIQLTDYGALTLDCSPRTGLDFNEMVLLTMEKKSWLVHKQWFLDLPLP

WTSGASTSQETWNRQDLLVTFKTAHAKKQEVVVLGSQEGAMHTALTGAT

EIQTSGTTTIFAGHLKCRLKMDKLTLKGMSYVMCTGSFKLEKEVAETQH

GTVLVQVKYEGTDAPCKIPFSSQDEKGVTQNGRLITANPIVTDKEKPVN

IEAEPPFGESYIVVGAGEKALKLSWFKKGSTLGKAFSTTLKGAQRLAAL

GDTAWDFGSIGGVENSIGKAVHQVFGGAFRTLFGGMSWITQGLMGALLL

WMGVNARDRSIALAFLATGGVLVFLATNVHA

In some embodiments, the modified forms of both the M and E structural proteins comprise one or more amino acid substitution of SEQ ID NO: 10, wherein SEQ ID NO: 10 comprises amino acids 206-676 of dengue virus type 2 polyprotein (strain 16681) (Genbank Accession No. U87411.1) and amino acids 695-794 of Japanese encephalitis (strain Nakayama; Genbank Accession No. EF571853.1) E structural protein.

(SEQ ID NO: 10)
SVALVPHVGMGLETRTETWMSSEGAWKHVQRIETWILRHPGFTMMAAIL

AYTIGTTHFQRALIFILLTAVTPSMTMRCIGMSNRDFVEGVSGGSWVDI

VLEHGSCVTTMAKNKPTLDFELIKTEAKQPATLRKYCIEAKLTNTTTES

RCPTQGEPSLNEEQDKRFVCKHSMVDRGWGNGCGLFGKGGIVTCAMFRC

KKNMEGKVVQPENLEYTIVITPHSGEEHAVGNDTGKHGKEIKITPQSSI

TEAELTGYGTVTMECSPRTGLDFNEMVLLQMENKAWLVHRQWFLDLPLP

WLPGADTQGSNWIQKETLVTFKNPHAKKQDVVVLGSQEGAMHTALTGAT

EIQMSSGNLLFTGHLKCRLRMDKLQLKGMSYSMCTGKFKVVKEIAETQH

GTIVIRVQYEGDGSPCKIPFEIMDLEKRHVLGRLITVNPIVTEKDSPVN

IEAEPPFGDSYIIIGVEPGQLKLNWFKKGSTLGKAFSTTLKGAQRLAAL

GDTAWDFGSIGGVFNSIGKAVHQVFGGAFRTLFGGMSWITQGLMGALLL

WMGVNARDRSIALAFLATGGVLVFLATNVHA

In some embodiments, the modified forms of both the M and E structural proteins comprise one or more amino acid substitution of SEQ ID NO: 12, wherein SEQ ID NO: 12 comprises amino acids 205-676 of dengue virus type 4 polyprotein (strain H-241) (Genbank Accession No. U18433.1) and amino acids 695-794 of Japanese encephalitis (strain Nakayama; Genbank Accession No. EF571853.1) E structural protein.

(SEQ ID NO: 12)
SVALAPHVGMGLDTRTQTWMSAEGAWRQVEKVETWALRHPGFTILALFL

AHYIGTSLTQKVVIFILLMLVTPSMTMRCVGVGNRDFVEGLSGATWVDV

VLEHGGCVTTMAKNKPTLDIELQKTEATQLATLRKLCIEGKITNITTDS

RCPTQGEAILPEEQDQNYVCKHTYVDRGWGNGCGLFGKGSLVTCAKFQC

LESIEGKVVQHENLKYTVIITVHTGDQHQVGNETQGVTAEITPQASTAE

VILPEYGTLGLECSPRTGLDFNEMISLTMKNKAWMVHRQWFFDLPLPWT

SGATAETPTWNRKELLVTFKNAHAKKQEVVVLGSQEGAMHTALTGATEI

QTSGGTSIFAGHLKCRLKMDKLELKGMSYAMCLSSFVLKKEVSETQHGT

ILIKVEYKGEDAPCKIPFSTEDGQGKAHNGRLITANPVVTKKEEPVNIE

AEPPFGESNIVIGIGDKALKINWYKKGSTLGKAFSTTLKGAQRLAALGD

TAWDFGSIGGVFNSIGKAVHQVFGGAFRTLFGGMSWITQGLMGALLLWM

GVNARDRSIALAFLATGGVLVFLATNVHA

In some embodiments, the modified forms of both the M and E structural proteins comprise one or more amino acid substitution of SEQ ID NO: 11, wherein SEQ ID NO: 11 comprises amino acids 206-674 of dengue virus type 3 polyprotein (strain 16562) (Genbank Accession No. KU725665.1) and amino acids 695-794 of Japanese encephalitis (strain Nakayama; Genbank Accession No. EF571853.1) E structural protein.

(SEQ ID NO: 11)

SVALTPHSGMGLETRAETWMSSEGAWKHAQRVESWILRNPGFALLAGFM

AYMIGQTGIQRTVFFVLMMLVAPSYGMRCVGVGNRDFVEGVSGGAWVDL

VLEHGGCVTTMAQGKPTLDFELIKTTAKEVALLRTYCIEASISNITTAT

RCPTQGEPYLKEEQDQQYICRRDVVDRGWGNGCGLFGKGGVVTCAKFSC

SGKITGNLVQIENLEYTVVVTVHNGDTHAVGNDISNHGVTATITPRSPS

VEVKLPDYGELTLDCEPRSGIDFNEMILMKMKKKTWLVHKQWFLDLPLP

WAAGADTSEVHWNYKERMVTFKVPHAKRQDVTVLGSQEGAMHSALTGAT

EVDSGDGNHMFAGHLKCKVRMEKLRIKGMSYTMCSGKFSIDKEMAETQH

GTTVVKVKYEGAGAPCKVPIEIRDVNKEKVVGRIISSTPFAEYTNSVTN

IELEPPFGDSYIVIGVGDSALTLHWFRKGSTLGKAFSTTLKGAQRLAAL

GDTAWDFGSIGGVFNSIGKAVHQVFGGAFRTLFGGMSWITQGLMGALLL

WMGVNARDRSIALAFLATGGVLVFLATNVHA

In some embodiments, Japanese encephalitis viral polypeptide corresponds to amino acids 695-794 of the E structural protein of Japanese encephalitis virus strain Nakayama (Genbank Accession No. EF571853.1).

(SEQ ID NO: 13)

TLGKAFSTTLKGAQRLAALGDTAWDFGSIGGVFNSIGKAVHQVFGGAFR

TLFGGMSWITQGLMGALLLWMGVNARDRSIALAFLATGGVLVFLATNVH

A

Furthermore, the pharmaceutically acceptable carrier and/or adjuvant can be, but are not limited to, AddaVax (InvivoGen). In addition to adjuvant or carrier, the pharmaceutical composition of the present disclosure may contain a single active ingredient or a combination of two or more active ingredients, as far as they are not contrary to the objects of the present disclosure. In a combination of plurality of active ingredients, contents or concentration of the respective ingredients in the disclosed composition may be suitably varied in different embodiments in consideration of their therapeutic effects and safety. The term "combination" used herein means two or more active ingredients are administered to a subject simultaneously in the form of a single entity or dosage, or those active ingredients are administered to a subject as separate entities either simultaneously or sequentially with no specific time limits, wherein such administration provides therapeutically effective levels of the two components in the body, preferably at the same time.

In the fourth aspect, the present disclosure provides a method of producing an antibody against a flavivirus or an antiserum containing a neutralizing antibody against a flavivirus comprising bringing a subject into contact with the virus-like particle provided in the first aspect of the present application and/or the nucleic acid molecule provided in the second aspect of the present disclosure in a manner which an immune response is elicited by such contact. The subject can be a mammal such as human. The antibody produced by the disclosed method may be used for passive immunization against a flavivirus-causing pathogen infecting other subjects or mammals by administering produced antibody with a therapeutically effective dosage to the mammal. The administered antibody is effective against the flavivirus infecting the mammal or subject thus preventing or curing the mammal from flavivirus infection or any diseased state caused by the flavivirus.

The antibody produced from other mammal other than human in the present disclosure can be further subjected to humanization process using alone or more conventionally known techniques. Thus, in more embodiment, the method provided in this aspect further comprises the step of humanizing a non-human mammal produced antibody. The antibody or humanized antibody acquired may be given to the human subject for preventing or eradicating flavivirus infection, treating or alleviating any diseased state or symptoms raised by flavivirus infection in the subject. Moreover, the antibody produced according to the disclosed method can be employed for in vitro selection of a subpopulation from immune cells such as B-cell and T-cell derived from the patient. The selected subpopulation immune cells are subsequently re-administered to the patient to boost immunity against flavivirus infection.

Further embodiments are directed to antiserum containing the disclosed antibodies obtainable by the conventional manner. Specifically, blood samples are taken from the immunized non-human animal, and the blood is processed to obtain the antiserum, i.e. the antibody-containing liquid component of the blood thereof. The non-human mammal is preferably selected from the group consisting of rat, mouse, hamster, pig, rabbit, horse, donkey, goat, sheep, guinea pig, lama, and non-human primate.

In the fifth aspect, the present disclosure set out a method of treating a disease or condition caused by flavivirus infection such as dengue fever in a subject. Preferably, the virus-like particle provided in the first aspect, the nucleotide molecule provided in the second aspect, or the composition provided in the third aspect is administered to the subject.

By administering the above modified virus-like particle, nucleotide molecule encoding the modified virus-like particle or vaccine composition to the subject, immune response or immunity against a flavivirus can be induced or enhanced or established in the subject. Thus, any diseased condition potentially caused by the flavivirus infection such as dengue infection can effectively be prevented or eradicated by the established immunity. In this aspect, the virus-like particle, nucleotide molecule or composition may be administered to the patient specifically to an affected organ or systemically to the general immune system of the subject boosting overall resistance against flavivirus infection.

Preferably, diseased state or symptoms caused by a flavivirus may be dengue, dengue fever, dengue haemorrhagic fever and severe dengue.

In further embodiments of the method treating flavivirus infection, the virus like particle can also be applied for immune therapy. The virus-like particle may be applied to ex vivo to cells derived from the patient or a human cell line which are subsequently administered to the patient.

In the sixth aspect, the present disclosure provides a method of producing the virus-like particle provided in the first aspect comprising culturing a cell which is expressing the virus-like particle from a gene encoding for the same; and recovering the virus-like particles from the cell culture. Various host-vector systems may be used in the disclosed method of producing the virus-like particle. Eukaryotic cells can be used for the method provided by the fourth aspect of the present application. Examples of eukaryotic cells include, but are not limited to, insect cells (e.g. C6/36, Sf9 cells, High five cells), yeast cells (e.g. *Saccharomyces cerevisiae*) and mammalian cells (e.g. CHO cells, human embryonic kidney 293F cells). Vector used for the method provided by the second aspect of the present application comprises a nucleic acid molecule encoding the virus-like particle to be expressed. Cells may be transfected with the vector using conventional methods (e.g. lipofection, electroporation). A skilled person can select culture medium. After the transfection, a stably protein-producing clone of transfected cells may be selected, and virus-like particle can be produced in the cells and released into culture media. Virus-like particle may be recovered from the culture media and purified using ultracentrifugation and/or chromatography. It is important to note that the expressed and recovered proteins or particles are mature virus-like particles, which cannot replicate in the subject being administrated with the recovered proteins and, therefore, can be safely applied as the vaccine composition.

The following examples are intended to further illustrate the disclosure, without any intent for the disclosure to be limited to the specific embodiments described therein.

Example 1

Expression of Flavivirus Structural Proteins

Dengue virus types 1-4 and Japanese encephalitis virus envelope glycoproteins were used as viral structural proteins in the present experiments. In the dengue virus structural proteins used, at least one modification or modified form was introduced by one or more approach known in the field. More specifically, conserved amino acid His at positions M7, E261, E282, and E317 of dengue virus sequence, are replaced by amino acid Ala at positions 7, 336, 357 and 392 in SEQ ID NO. 1-3, or conserved amino acid His at positions M7, E259, E280 and E315 of dengue virus sequence or wild type are replaced by amino acid Ala at positions 7, 334, 355 and 390 in SEQ ID NO. 4. In further embodiments of the experiments conducted, the modified form further comprises replacement of conserved amino acid His at positions E27, E149 and E209 of dengue virus sequence or wild type with amino acid Asn at positions 102, 224 and 284 in SEQ ID NO. 1-3 or replacement of conserved amino acid His at positions E27, E149 and E207 of dengue virus sequence or wild type with amino acid Asn at positions 102, 224 and 282 in SEQ ID NO. 4. Still in some embodiment of the experiments performed, more modifications were made to any one or a combination of replacing an amino acid Ser or Glu at position E186 of dengue virus sequence or amino acid Ser at position E184 of dengue virus sequence or wild type with amino acid Phe at position 261 in SEQ ID NO. 1-3 or at position 259 in SEQ ID NO. 4, respectively, replacing of amino acid Arg located at position E188 of dengue virus sequence or position E186 of dengue virus sequence with amino acid Leu at position 263 in SEQ ID NO. 1-3 or at position 261 in SEQ ID NO. 4, substituting of amino acid Asn or Val at position E242 of dengue virus sequence or amino acid Asn at position E240 of dengue virus sequence with amino acid Ser at position 317 in SEQ ID NO. 2-3 or position 315 in SEQ ID NO. 4, altering of amino acid Arg or Lys located at position E323 of dengue virus sequence or amino acid Lys position E321 of dengue virus sequence or wild type with amino acid Gln at position 398 of SEQ ID NO. 2-3 or position 396 of SEQ ID NO. 4. Some embodiments of the modified viral structural protein studied in the present experiments were listed in Table 1 below.

| Position in this construct | | Position in the wild type virus protein | | DENV-1 | | DENV-2 | | DENV-3 | | DENV-4 | |
|---|---|---|---|---|---|---|---|---|---|---|---|
| DENV-1, -2 and -4 | DENV-3 | DENV-1, -2 and -4 | DENV-3 | Wild type | Virus-like particle | Wild type | Virus-like particle | Wild type | Virus-like particle | Wild type | Virus-like particle |
| 7 | 7 | M 7 | M 7 | His | Ala | His | Ala | His | Ala | His | Ala |
| 102 | 102 | E 27 | E 27 | His | Asn | His | Asn | His | Asn | His | Asn |
| 224 | 224 | E 149 | E 149 | His | Asn | His | Asn | His | Asn | His | Asn |
| 261 | 259 | E 186 | E 184 | Ser | Phe | Ser | Phe | Ser | Phe | Glu | Phe |
| 263 | 261 | E 188 | E 186 | Arg | Leu | Arg | Leu | Arg | Leu | Arg | Leu |
| 284 | 282 | E 209 | E 207 | His | Asn | His | Asn | His | Asn | His | Asn |
| 317 | 315 | E 242 | E 240 | Thr | Thr | Asn | Ser | Asn | Ser | Val | Ser |
| 336 | 334 | E 261 | E 259 | His | Ala | His | Ala | His | Ala | His | Ala |
| 357 | 355 | E 282 | E 280 | His | Ala | His | Ala | His | Ala | His | Ala |
| 392 | 390 | E 317 | E 315 | His | Ala | His | Ala | His | Ala | His | Ala |
| 398 | 396 | E 323 | E 321 | Gln | Gln | Arg | Gln | Lys | Gln | Lys | Gln |

To express the one or more modified viral structural proteins in insect cells, an M-E expression vector was transfected to C6/36 or Sf9 cells. After the transfection, intracellular E expression was examined in an indirect immunofluorescence assay, by using an anti-Dengue virus monoclonal antibody (clone 1D10) that specifically binds to the E protein and Cy3-conjugated goat anti-mouse Ig antibodies as the secondary antibody. The results are shown in FIG. 9.

Extracellular level of the E protein was assessed in a capture ELISA. Culture media from the transfected cells were harvested and the expression of the E protein was examined by using Dengue virus monoclonal antibody as the primary antibody and horse radish peroxidase-conjugated rabbit anti-mouse IgG antibody as the secondary antibody. Results are shown in Table 2 below.

| | Extracellular E protein concentration at indicated hour after transfection (μg/ml) | | |
|---|---|---|---|
| Construct | 0 hr | 24 hr | 48 hr |
| Plasmid construct #1 | 0.097 | 0.172 | 0.386 |
| Plasmid construct #2 | 0.014 | 0.171 | 0.381 |

Example 2

Preparation of a Virus-Like Particle from Stably Flavivirus Structural Proteins-Expressing Cells Expression vector for flavivirus M and E structural proteins used in Example 1 were used. In the same manner as Example 1, the vector was transfected to C6/36 or Sf9 cells. In the generation of stably expressing transfectants, the vector was transfected into the cells, and the recombinant transfected cells were selected with the use of blasticidin. Clones of drug-resistant transfectant were selected based on intracellular and extracellular expression of dengue virus E protein, employing a murine monoclonal antibody, 1D10, in indirect immunofluorescence and dot blot immunoassay formats. A transfectant clone with high level of extracellular E protein expression was expanded. Cell culture media were concentrated, and then subjected to purification by ultracentrifugation in sucrose gradient and/or potassium tartrate—glycerol gradient as described previously (Charoensri et al, 2014). The presence of the two envelope proteins, E and M, in the virus-like particle preparations was assessed by sodium dodecyl sulfate-polyacrylamide gel electrophoresis and silver staining. The results are shown in FIG. 10.

Morphological assessment was performed by negative staining using uranyl acetate and transmission electron microscopy. The results are shown in FIG. 11. In the purified particulate fraction, generally round particles with some variations in size and shape, as expected from virus-like particles without the core structure, were observed.

Example 3

Antibody Against Dengue Virus in Mice

Purified dengue virus-like particles obtained in Example 2 was used in this example. Six mice were immunized with 1 μg of the DENV-2 virus-like particles in 20% glycerol-NTE buffer (12 mM Tris [pH 8.0], 1 mM EDTA and 120 mM NaCl) containing Squalene-oil-in-water adjuvant (AddaVax, InvivoGen) by subcutaneous injection at weeks 0 and 8. The serum was assayed for neutralizing antibody to DENV-2 by employing a prototypic DENV-2 strain 16681. Anti-DENV neutralizing antibodies in the immunized mice sera were detected by a plaque reduction neutralization test (PRNT) on Vero cells. The endpoint titer was calculated as the highest serum dilution tested that reduced the number of plaques forming unit by at least 50% (PRNT50). The results are shown in FIG. 12. The virus-like particles were able to induce high levels of neutralizing antibodies in immunized mice.

Example 4

Antibody Against Dengue Virus in Monkeys

Purified dengue virus-like particle obtained in Example 2 was used in this example. Six cynomolgus macaques were immunized with monovalent live-attenuated dengue virus at day 0. They were boosted with the 10 μg of virus-like particles in 20% glycerol-NTE buffer (12 mM Tris [pH 8.0], 1 mM EDTA and 120 mM NaCl) containing Squalene-oil-in-water adjuvant (AddaVax, InvivoGen) by subcutaneous injection twice on days 60 and 90. Macaques were then challenged with a DENV-2 wild type virus on day 120. The sera were assayed for neutralizing antibody to DENV-2 employing a DENV-2 prototypic strain 16681 and Vero cells in a plaque reduction neutralization test (PRNT). The endpoint titer was calculated as the highest serum dilution tested that reduced the number of plaques forming unit by at least 50% (PRNT50). The results are shown in FIG. 13. The virus-like particles were able to induce high levels of neutralizing antibodies to DENV-2 in live attenuated virus-primed macaques and protected them from infection following challenge with a DENV-2 wild type virus.

Example 5

Preparation of a Pharmaceutical Composition Comprising Dengue Virus-Like Particle Dengue virus-like particles were prepared according to Example 2. To prepare a pharmaceutical composition which is a vaccine composition, 10 μg of purified virus-like particles were mixed with 0.1 ml of NTE buffer containing 12 mM Tris (pH 8.0), 1 mM EDTA and 120 mM NaCl.

It is to be understood that the present disclosure may be embodied in other specific forms and is not limited to the embodiments described above. However, modification and equivalents of the disclosed concepts such as those which readily occur to one skilled in the art are intended to be included within the scope of the claims which are appended thereto.

REFERENCES

Allison S L, Stadler K, Mandl C W, Kunz C, Heinz F X. Synthesis and secretion of recombinant tick-borne encephalitis virus protein e in soluble and particulate form. J Virol 1995; 69: 5816-20.

Capeding M R, Tran N H, Hadinegoro S R, Ismail H I, Chotpitayasunondh T, Chua M N, et al. Clinical efficacy and safety of a novel tetravalent dengue vaccine in healthy children in Asia: a phase 3, randomised, observer-masked, placebo-controlled trial. Lancet 2014; 384: 1358-65.

Chan, A. H., Tan, H. C., Chow, A. Y., Lim, A. P., Lok, S. M., Moreland, N. J., et al. A human prM antibody that recognizes a novel cryptic epitope on dengue E glycoprotein. PLOS ONE 2012; 7: e33451.

Charoensri N, Suphatrakul A, Sriburi R, Yasanga T, Junjhon J, Keelapang P, et al. An optimized expression vector for improving the yield of dengue virus-like particles from transfected insect cells. J Virol Methods 2014: 205: 116-23.

Chaudhury S, Ripoll D R, Wallqvist A. Structure-based pKa prediction provides a thermodynamic basis for the role of histidines in pH-induced conformational transitions in dengue virus. Biochem Biophys Rep 2015; 4: 375-85.

Christian E A, Kahle K M, Mattia K, Puffer B A, Pfaff J M, Miller A, et al. Atomic-level functional model of dengue virus envelope protein infectivity. Proc Natl Acad Sci (USA) 2013; 110: 18662-7.

Dejnirattisai W, Jumnainsong A, Onsirisakul N, Fitton P, Vasanawathana S, Limpitikul W, et al. Cross-reacting antibodies enhance dengue virus infection in humans. Science 2010; 328: 745-8.

Dejnirattisai W, Wongwiwat W, Supasa S, Zhang X K, Dai X H, Rouvinsky A, et al. A new class of highly potent, broadly neutralizing antibodies isolated from viremic patients infected with dengue virus. Nat Immunol 2015; 16: 170-7.

Flipse J, Smit J M. The complexity of a dengue vaccine: a review of the human antibody response. PLOS Negl Trop Dis 2015; 9: e0003749.

Fritz R, Stiasny K, Heinz F X. Identification of specific histidines as pH sensors in flavivirus membrane fusion. J Cell Biol 2008; 183: 353-61.

Fuzo C A, Degrève L. The pH dependence of flavivirus envelope protein structure: insights from molecular dynamics simulations, J Biomolecular Structure Dynamics 2014; 32: 1563-74.

Hadinegoro S R, Arredondo-Garcia J L, Capeding M R, Deseda C, Chotpitayasunondh T, Dietze R, et al. Efficacy and long-term safety of a dengue vaccine in regions of endemic disease. N Engl J Med 2015; 373: 1195-206.

Hsieh S C, Tsai W Y, Nerurkar V R, Wang W K. Characterization of the ectodomain of the envelope protein of dengue virus type 4: expression, membrane association, secretion and particle formation in the absence of precursor membrane protein. PLOS ONE 2014; 9: e100641.

Huang K J, Yang Y C, Lin Y S, Huang J H, Liu H S, Yeh T M, et al. The dual-specific binding of dengue virus and its target cells for the antibody-dependent enhancement of dengue virus infection. J Immunol 2006; 176: 2825-32.

Huang K J, Cheng Y T, Lin Y S, Huang J H, Liu H S, Yeh T M, et al. Anti-prM antibody as an autoantibody in dengue virus infection. Am J Infect Dis 2008; 4: 59-67.

Junjhon J, Lausumpao M, Supasa S, Noisakran S, Songjaeng A, Saraithong P, et al. Differential modulation of prM cleavage, extracellular particle distribution, and virus infectivity by conserved residues at nonfurin consensus positions of the dengue pr-M junction. J Virol 2008; 82: 10776-91.

Junjhon J, Edwards T J, Utaipat U, Bowman V D, Holdaway H A, Zhang W, et al. Influence of pr-M cleavage on the heterogeneity of extracellular dengue virus particles. J Virol 2010; 84: 8353-8.

Kampmann T, Mueller D S, Mark A E, Young P R, Kobe B. The role of histidine residues in low pH-mediated viral membrane fusion. Structure 2006; 14: 1481-7.

Katzelnick L C, Gresh L, Halloran M E, Mercado J C, Kuan G, Gordon A, et al. Antibody-dependent enhancement of severe dengue disease in humans. Science 2017; 358: 929-32.

Konishi E, Fujii A, Mason P M. Generation and characterization of a mammalian cell line continuously expressing Japanese encephalitis virus subviral particles. J Virol 2001; 75: 2204-12.

Konishi E, Fujii A. Dengue type 2 virus subviral extracellular particles produced by a stably transfected mammalian cell line and their evaluation for a subunit vaccine. Vaccine 2002; 20: 1058-67.

Konishi E, Mason P W. Proper maturation of the Japanese encephalitis virus envelope glycoprotein requires cosynthesis with the premembrane protein. J Virol 1993; 67: 1672-5.

Kuhn R J, Zhang W, Rossmann M G, Pletnev S V, Corver J, Lenches E, et al. Structure of dengue virus: implications for flavivirus organization, maturation, and fusion. Cell 2002; 108: 717-25.

Li L, Lok S M, Yu I M, Zhang Y, Kuhn R J, Chen J, et al. The flavivirus precursor membrane-envelope protein complex: structure and maturation. Science 2008; 319: 1830-4.

Lok S M. The interplay of dengue virus morphological diversity and human antibodies. Tr Microbiol 2016; 24: 284-93.

Lorenz I C, Allison S L, Heinz F X, Helenius A. Folding and dimerization of tick-borne encephalitis virus envelope proteins prM and E in the endoplasmic reticulum. J Virol 2002; 76: 5480-91.

Luo Y Y, Feng J J, Zhou J M, Yu Z Z, Fang D Y, Yan H J, et al. Identification of a novel infection-enhancing epitope on dengue prM using a dengue cross-reacting monoclonal antibody. BMC Microbiology 2013; 13: 194.

Luo Y, Guo X, Yan H, Fang D, Zeng G, Zhou J, et al. Comprehensive mapping infection-enhancing epitopes of dengue pr protein using polyclonal antibody against prM. Appl Microbiol Biotechnol 2015; 99: 5917-27.

Mueller D S, Kampmann T, Yennamalli R, Young P R, Kobe B, Mark A E. Histidine protonation and the activation of viral fusion proteins. Biochem Soc T 2008; 36: 43-5.

Nelson S, Poddar S, Lin T-Y, Pierson T C. Protonation of individual histidine residues is not required for the pH-dependent entry of West Nile virus: evaluation of the "histidine switch" hypothesis. J Virol 2009; 83: 12631-5.

Plevka P, Battisti A J, Junjhon J, Winkler D C, Holdaway H A, Keelapang P, et al. Maturation of flaviviruses starts from one or more icosahedrally independent nucleation centers. EMBO Reports 2011; 12: 602-6.

Plevka P, Battisti A J, Sheng J, Rossmann M G. Mechanism for maturation-related reorganization of flavivirus glycoproteins. J Structural Biol 2014; 185: 27-31.

Purdy D E, Chang G J J. Secretion of noninfectious dengue virus-like particles and identification of amino acids in the stem region involved in intracellular retention of envelope protein. Virology 2005; 333:239-50.

Richter M K, da Silva Voorham J M, Torres Pedraza S, Hoornweg T E, van de Pol D P, Rodenhuis-Zybert I A, et al. Immature dengue virus is infectious in human immature dendritic cells via interaction with the receptor molecule D C-SIGN. PLOS One 2014; 9: e98785.

Rodenhuis-Zybert I A, van der Schaar H M, da Silva Voorham J M, van der Ende-Metselaar H, Lei H Y, Wilschut J, et al. Immature dengue virus: a veiled pathogen? PLOS Pathog 2010; 6: e1000718.

Rouvinski A, Guardado-Calvo P, Barba-Spaeth G, Duquerroy S, Vaney M C, Kikuti C, et al. Recognition determinants of broadly neutralizing human antibodies against dengue viruses. Nature 2015; 520: 109-13.

Sabchareon A, Wallace D, Sirivichayakul C, Limkittikul K, Chanthavanich P, Suvannadabba S, et al. Protective efficacy of the recombinant, live-attenuated, CYD tetravalent dengue vaccine in Thai schoolchildren: a randomised, controlled phase 2b trial. Lancet 2012; 380: 1559-67.

Suphatrakul A, Yasanga T, Keelapang P, Sriburi R, Roytrakul T, Pulmanausahakul R, et al. Generation and preclinical immunogenicity study of dengue type 2 virus-like particles derived from stably transfected mosquito cells. Vaccine 2015; 33: 5613-22.

Shang W, Liu J, Yang J, Hu Z, Rao X. Dengue virus-like particles: construction and application. Appl Micrbiol Biotechnol 2012; 94: 36-46.

Smith S A, Nivarthi U K, de Alwis R, Kose N, Sapparapu G, Bombardi R, et al. Dengue virus prM-specific human monoclonal antibodies with virus replication enhancing properties recognize a single immunodominant antigenic site. J Virol 2016; 90: 780-9.

Song K Y, Zhao H, Li S H, Li X F, Deng Y Q, Wang H J, et al. Identification and characterization of a linearized B-cell epitope on the pr protein of dengue virus. J Gen Virol 2013; 94: 1510-6.

Trainor N B, Crill W D, Roberson J A, Chang G J. Mutation analysis of the fusion domain region of St. Louis encephalitis virus envelope protein. Virology 2007; 360: 398-406.

Urakami A, Ngwe Tun M M, Moi M L, Sakurai A, Ishikawa M, Kuno S, et al. An envelope-modified tetravalent dengue virus-like-particle vaccine has implications for flavivirus vaccine design. J Virol 2017; 91: e01181-17. doi: 10.1128/JVI.01181-17.

Villar L, Dayan G H, Arredondo-Garcia J L, Rivera D M, Cunha R, Deseda C, et al. Efficacy of a tetravalent dengue vaccine in children in Latin America. N Engl J Med 2015; 372: 113-23.

Wang Z, Li L, Pennington J G, Sheng J, Yap M L, Plevka P, et al. Obstruction of dengue virus maturation by fab fragments of the 2H2 antibody. J Virol 2013; 87: 8909-15.

Yamaji H. Suitability and perspectives on using recombinant insect cells for the production of virus-like particles. Appl Microbiol Biotechnol 2014; 98: 1963-70.

Yu I M, Zhang W, Holdaway H A, Li L, Kostyuchenko V A, Chipman P R, et al. Structure of the immature dengue virus at low pH primes proteolytic maturation. Science 2008; 319: 1834-7.

Zhang Y, Corver J, Chipman P R, Zhang W, Plevnev S V, Sedlak D, et al. Structures of immature flavivirus particles. EMBO J 2003; 22: 2604-13.

Zhang X, Ge P, Yu X, Brannan J M, Bi G, Zhang Q, et al. Cryo-E M structure of the mature dengue virus at 3.5-A resolution. Nat Struct Mol Biol 2013; 20: 105-10.

Zheng A, Umashankar M, Kielian M. In vitro and in vivo studies identify important features of dengue virus pr-E protein interactions. PLOS Pathogens 2010; 6: e1001157.

Zheng A, Yuan F, Kleinfelter L M, Kielian M. A toggle switch controls the low pH-triggered rearrangement and maturation of the dengue virus envelope proteins. Nat Comm 2014; 5: 3877.

---

SEQUENCE LISTING

<160> NUMBER OF SEQ ID NOS: 13

<210> SEQ ID NO 1
<211> LENGTH: 570
<212> TYPE: PRT
<213> ORGANISM: Dengue virus

<400> SEQUENCE: 1

```
Ser Val Ala Leu Ala Pro Ala Val Gly Leu Gly Leu Glu Thr Arg Thr
1               5                   10                  15

Glu Thr Trp Met Ser Ser Glu Gly Ala Trp Lys Gln Ile Gln Arg Val
            20                  25                  30

Glu Thr Trp Ala Leu Arg His Pro Gly Phe Thr Val Ile Ala Leu Phe
        35                  40                  45

Leu Ala His Ala Ile Gly Thr Ser Ile Thr Gln Lys Gly Ile Ile Phe
    50                  55                  60

Ile Leu Leu Met Leu Val Thr Pro Ser Met Ala Met Arg Cys Val Gly
65                  70                  75                  80

Ile Gly Ser Arg Asp Phe Val Glu Gly Leu Ser Gly Ala Thr Trp Val
                85                  90                  95

Asp Val Val Leu Glu Asn Gly Ser Cys Val Thr Thr Met Ala Lys Asp
            100                 105                 110

Lys Pro Thr Leu Asp Ile Glu Leu Leu Lys Thr Glu Val Thr Asn Pro
        115                 120                 125

Ala Val Leu Arg Lys Leu Cys Ile Glu Ala Lys Ile Ser Asn Thr Thr
    130                 135                 140

Thr Asp Ser Arg Cys Pro Thr Gln Gly Glu Ala Thr Leu Val Glu Glu
145                 150                 155                 160

Gln Asp Ala Asn Phe Val Cys Arg Arg Thr Phe Val Asp Arg Gly Trp
                165                 170                 175
```

Gly Asn Gly Cys Gly Leu Phe Gly Lys Gly Ser Leu Leu Thr Cys Ala
            180                 185                 190

Lys Phe Lys Cys Val Thr Lys Leu Glu Gly Lys Ile Val Gln Tyr Glu
        195                 200                 205

Asn Leu Lys Tyr Ser Val Ile Val Thr Val His Thr Gly Asp Gln Asn
    210                 215                 220

Gln Val Gly Asn Glu Ser Thr Glu His Gly Thr Ala Thr Ile Thr
225                 230                 235                 240

Pro Gln Ala Pro Thr Thr Glu Ile Gln Leu Thr Asp Tyr Gly Ala Leu
                245                 250                 255

Thr Leu Asp Cys Phe Pro Leu Thr Gly Leu Asp Phe Asn Glu Met Val
            260                 265                 270

Leu Leu Thr Met Lys Glu Lys Ser Trp Leu Val Asn Lys Gln Trp Phe
        275                 280                 285

Leu Asp Leu Pro Leu Pro Trp Thr Ser Gly Ala Ser Thr Ser Gln Glu
    290                 295                 300

Thr Trp Asn Arg Gln Asp Leu Leu Val Thr Phe Lys Thr Ala His Ala
305                 310                 315                 320

Lys Lys Gln Glu Val Val Leu Gly Ser Gln Glu Gly Ala Met Ala
                325                 330                 335

Thr Ala Leu Thr Gly Ala Thr Glu Ile Gln Thr Ser Gly Thr Thr Thr
            340                 345                 350

Ile Phe Ala Gly Ala Leu Lys Cys Arg Leu Lys Met Asp Lys Leu Thr
        355                 360                 365

Leu Lys Gly Met Ser Tyr Val Met Cys Thr Gly Ser Phe Lys Leu Glu
    370                 375                 380

Lys Glu Val Ala Glu Thr Gln Ala Gly Thr Val Leu Val Gln Ile Lys
385                 390                 395                 400

Tyr Glu Gly Thr Asp Ala Pro Cys Lys Ile Pro Phe Ser Thr Gln Asp
                405                 410                 415

Glu Lys Gly Val Thr Gln Asn Gly Arg Leu Ile Thr Ala Asn Pro Ile
            420                 425                 430

Val Thr Asp Lys Glu Lys Pro Val Asn Ile Glu Ala Glu Pro Pro Phe
        435                 440                 445

Gly Glu Ser Tyr Ile Val Ile Gly Ala Gly Glu Lys Ala Leu Lys Leu
    450                 455                 460

Ser Trp Phe Lys Lys Gly Ser Thr Leu Gly Lys Ala Phe Ser Thr Thr
465                 470                 475                 480

Leu Lys Gly Ala Gln Arg Leu Ala Ala Leu Gly Asp Thr Ala Trp Asp
                485                 490                 495

Phe Gly Ser Ile Gly Gly Val Phe Asn Ser Ile Gly Lys Ala Val His
            500                 505                 510

Gln Val Phe Gly Gly Ala Phe Arg Thr Leu Phe Gly Gly Met Ser Trp
        515                 520                 525

Ile Thr Gln Gly Leu Met Gly Ala Leu Leu Leu Trp Met Gly Val Asn
    530                 535                 540

Ala Arg Asp Arg Ser Ile Ala Leu Ala Phe Leu Ala Thr Gly Gly Val
545                 550                 555                 560

Leu Val Phe Leu Ala Thr Asn Val His Ala
                565                 570

<210> SEQ ID NO 2
<211> LENGTH: 570

<212> TYPE: PRT
<213> ORGANISM: Dengue virus

<400> SEQUENCE: 2

```
Ser Val Ala Leu Val Pro Ala Val Gly Met Gly Leu Glu Thr Arg Thr
1               5                   10                  15

Glu Thr Trp Met Ser Ser Glu Gly Ala Trp Lys His Ala Gln Arg Ile
            20                  25                  30

Glu Thr Trp Ile Leu Arg His Pro Gly Phe Thr Ile Met Ala Ala Ile
            35                  40                  45

Leu Ala Tyr Thr Ile Gly Thr Thr His Phe Gln Arg Val Leu Ile Phe
        50                  55                  60

Ile Leu Leu Thr Ala Val Ala Pro Ser Met Thr Met Arg Cys Ile Gly
65                  70                  75                  80

Ile Ser Asn Arg Asp Phe Val Glu Gly Val Ser Gly Gly Ser Trp Val
                85                  90                  95

Asp Ile Val Leu Glu Asn Gly Ser Cys Val Thr Thr Met Ala Lys Asn
            100                 105                 110

Lys Pro Thr Leu Asp Phe Glu Leu Ile Lys Thr Glu Ala Lys Gln Pro
        115                 120                 125

Ala Thr Leu Arg Lys Tyr Cys Ile Glu Ala Lys Leu Thr Asn Thr Thr
    130                 135                 140

Thr Glu Ser Arg Cys Pro Thr Gln Gly Glu Pro Ser Leu Lys Glu Glu
145                 150                 155                 160

Gln Asp Lys Arg Phe Val Cys Lys His Ser Met Val Asp Arg Gly Trp
                165                 170                 175

Gly Asn Gly Cys Gly Leu Phe Gly Lys Gly Ile Val Thr Cys Ala
            180                 185                 190

Met Phe Thr Cys Lys Lys Asn Met Glu Gly Lys Ile Val Gln Pro Glu
        195                 200                 205

Asn Leu Glu Tyr Thr Ile Val Val Thr Pro His Ser Gly Glu Glu Asn
    210                 215                 220

Ala Val Gly Asn Asp Thr Gly Lys His Gly Lys Glu Ile Lys Val Thr
225                 230                 235                 240

Pro Gln Ser Ser Ile Thr Glu Ala Glu Leu Thr Gly Tyr Gly Thr Val
                245                 250                 255

Thr Met Glu Cys Phe Pro Leu Thr Gly Leu Asp Phe Asn Glu Met Val
            260                 265                 270

Leu Leu Gln Met Glu Asn Lys Ala Trp Leu Val Asn Arg Gln Trp Phe
        275                 280                 285

Leu Asp Leu Pro Leu Pro Trp Leu Pro Gly Ala Asp Lys Gln Glu Ser
    290                 295                 300

Asn Trp Ile Gln Lys Glu Thr Leu Val Thr Phe Lys Ser Pro His Ala
305                 310                 315                 320

Lys Lys Gln Asp Val Val Val Leu Gly Ser Gln Glu Gly Ala Met Ala
                325                 330                 335

Thr Ala Leu Thr Gly Ala Thr Glu Ile Gln Met Ser Ser Gly Asn Leu
            340                 345                 350

Leu Phe Thr Gly Ala Leu Lys Cys Arg Leu Arg Met Asp Lys Leu Gln
        355                 360                 365

Leu Lys Gly Met Ser Tyr Ser Met Cys Thr Gly Lys Phe Lys Val Val
    370                 375                 380

Lys Glu Ile Ala Glu Thr Gln Ala Gly Thr Ile Val Ile Gln Val Gln
385                 390                 395                 400
```

Tyr Glu Gly Asp Gly Ser Pro Cys Lys Ile Pro Phe Glu Ile Met Asp
                405                 410                 415

Leu Glu Lys Arg Tyr Val Leu Gly Arg Leu Ile Thr Val Asn Pro Ile
            420                 425                 430

Val Thr Glu Lys Asp Ser Pro Val Asn Ile Glu Ala Glu Pro Pro Phe
        435                 440                 445

Gly Asp Ser Tyr Ile Ile Ile Gly Val Glu Pro Gly Gln Leu Lys Leu
    450                 455                 460

Asn Trp Phe Lys Lys Gly Ser Thr Leu Gly Lys Ala Phe Ser Thr Thr
465                 470                 475                 480

Leu Lys Gly Ala Gln Arg Leu Ala Ala Leu Gly Asp Thr Ala Trp Asp
                485                 490                 495

Phe Gly Ser Ile Gly Gly Val Phe Asn Ser Ile Gly Lys Ala Val His
            500                 505                 510

Gln Val Phe Gly Gly Ala Phe Arg Thr Leu Phe Gly Gly Met Ser Trp
        515                 520                 525

Ile Thr Gln Gly Leu Met Gly Ala Leu Leu Leu Trp Met Gly Val Asn
    530                 535                 540

Ala Arg Asp Arg Ser Ile Ala Leu Ala Phe Leu Ala Thr Gly Gly Val
545                 550                 555                 560

Leu Val Phe Leu Ala Thr Asn Val His Ala
                565                 570

<210> SEQ ID NO 3
<211> LENGTH: 570
<212> TYPE: PRT
<213> ORGANISM: Dengue virus

<400> SEQUENCE: 3

Ser Val Ala Leu Thr Pro Ala Ser Gly Met Gly Leu Glu Thr Arg Ala
1               5                   10                  15

Glu Thr Trp Met Ser Ser Glu Gly Ala Trp Lys His Ala Gln Arg Val
            20                  25                  30

Glu Ser Trp Ile Leu Arg Asn Pro Gly Phe Ala Leu Leu Ala Gly Phe
        35                  40                  45

Met Ala Tyr Met Ile Gly Gln Thr Gly Ile Gln Arg Thr Val Phe Phe
    50                  55                  60

Val Leu Met Met Leu Val Ala Pro Ser Tyr Gly Met Arg Cys Val Gly
65                  70                  75                  80

Val Gly Asn Arg Asp Phe Val Glu Gly Val Ser Gly Gly Ala Trp Val
                85                  90                  95

Asp Leu Val Leu Glu Asn Gly Gly Cys Val Thr Thr Met Ala Gln Gly
            100                 105                 110

Lys Pro Thr Leu Asp Phe Glu Leu Thr Lys Thr Thr Ala Lys Glu Val
        115                 120                 125

Ala Leu Leu Arg Thr Tyr Cys Ile Glu Ala Ser Ile Ser Asn Ile Thr
    130                 135                 140

Thr Ala Thr Arg Cys Pro Thr Gln Gly Glu Pro Tyr Leu Lys Glu Glu
145                 150                 155                 160

Gln Asp Gln Gln Tyr Ile Cys Arg Arg Asp Val Val Asp Arg Gly Trp
                165                 170                 175

Gly Asn Gly Cys Gly Leu Phe Gly Lys Gly Val Val Thr Cys Ala
            180                 185                 190

Lys Phe Ser Cys Ser Gly Lys Ile Thr Gly Asn Leu Val Gln Ile Glu

```
              195                 200                 205
Asn Leu Glu Tyr Thr Val Val Thr Val His Asn Gly Asp Thr Asn
210                 215                 220

Ala Val Gly Asn Asp Thr Ser Asn His Gly Val Thr Ala Met Ile Thr
225                 230                 235                 240

Pro Arg Ser Pro Ser Val Glu Val Lys Leu Pro Asp Tyr Gly Glu Leu
                245                 250                 255

Thr Leu Asp Cys Phe Pro Leu Ser Gly Ile Asp Phe Asn Glu Met Ile
            260                 265                 270

Leu Met Lys Met Lys Lys Thr Trp Leu Val Asn Lys Gln Trp Phe
        275                 280                 285

Leu Asp Leu Pro Leu Pro Trp Thr Ala Gly Ala Asp Thr Ser Glu Val
290                 295                 300

His Trp Asn Tyr Lys Glu Arg Met Val Thr Phe Lys Ser Pro His Ala
305                 310                 315                 320

Lys Arg Gln Asp Val Thr Val Leu Gly Ser Gln Glu Gly Ala Met Ala
                325                 330                 335

Ser Ala Leu Ala Gly Ala Thr Glu Val Asp Ser Gly Asp Gly Asn His
            340                 345                 350

Met Phe Ala Gly Ala Leu Lys Cys Lys Val Arg Met Glu Lys Leu Arg
        355                 360                 365

Ile Lys Gly Met Ser Tyr Thr Met Cys Ser Gly Lys Phe Ser Ile Asp
370                 375                 380

Lys Glu Met Ala Glu Thr Gln Ala Gly Thr Thr Val Gln Val Lys
385                 390                 395                 400

Tyr Glu Gly Ala Gly Ala Pro Cys Lys Val Pro Ile Glu Ile Arg Asp
                405                 410                 415

Val Asn Lys Glu Lys Val Val Gly Arg Ile Ile Ser Ser Thr Pro Leu
            420                 425                 430

Ala Glu Asn Thr Asn Ser Val Thr Asn Ile Glu Leu Glu Pro Pro Phe
        435                 440                 445

Gly Asp Ser Tyr Ile Val Ile Gly Val Gly Asn Ser Ala Leu Thr Leu
450                 455                 460

His Trp Phe Arg Lys Gly Ser Thr Leu Gly Lys Ala Phe Ser Thr Thr
465                 470                 475                 480

Leu Lys Gly Ala Gln Arg Leu Ala Ala Leu Gly Asp Thr Ala Trp Asp
                485                 490                 495

Phe Gly Ser Ile Gly Gly Val Phe Asn Ser Ile Gly Lys Ala Val His
            500                 505                 510

Gln Val Phe Gly Gly Ala Phe Arg Thr Leu Phe Gly Gly Met Ser Trp
        515                 520                 525

Ile Thr Gln Gly Leu Met Gly Ala Leu Leu Leu Trp Met Gly Val Asn
530                 535                 540

Ala Arg Asp Arg Ser Ile Ala Leu Ala Phe Leu Ala Thr Gly Gly Val
545                 550                 555                 560

Leu Val Phe Leu Ala Thr Asn Val His Ala
                565                 570

<210> SEQ ID NO 4
<211> LENGTH: 568
<212> TYPE: PRT
<213> ORGANISM: Dengue virus

<400> SEQUENCE: 4
```

```
Ser Val Ala Leu Ala Pro Ala Val Gly Met Gly Leu Asp Thr Arg Thr
  1               5                  10                 15
Gln Thr Trp Met Ser Ala Glu Gly Ala Trp Arg Gln Val Glu Lys Val
            20                  25                  30
Glu Thr Trp Ala Leu Arg His Pro Gly Phe Thr Ile Leu Ala Leu Phe
            35                  40                  45
Leu Ala His Tyr Ile Gly Thr Ser Leu Thr Gln Lys Val Val Ile Phe
 50                  55                  60
Ile Leu Leu Met Leu Val Thr Pro Ser Met Thr Met Arg Cys Val Gly
 65                  70                  75                  80
Val Gly Asn Arg Asp Phe Val Glu Gly Leu Ser Gly Ala Thr Trp Val
                85                  90                  95
Asp Val Val Leu Glu Asn Gly Gly Cys Val Thr Thr Met Ala Lys Asn
                100                 105                 110
Lys Pro Thr Leu Asp Ile Glu Leu Gln Lys Thr Glu Ala Thr Gln Leu
            115                 120                 125
Ala Thr Leu Arg Lys Leu Cys Ile Glu Gly Lys Ile Thr Asn Ile Thr
 130                 135                 140
Thr Asp Ser Arg Cys Pro Thr Gln Gly Glu Ala Ala Leu Pro Glu Glu
 145                 150                 155                 160
Gln Asp Gln Asn Tyr Val Cys Lys His Thr Tyr Val Asp Arg Gly Trp
                165                 170                 175
Gly Asn Gly Cys Gly Leu Phe Gly Lys Gly Ser Leu Val Thr Cys Ala
                180                 185                 190
Lys Phe Gln Cys Leu Glu Pro Ile Glu Gly Lys Val Val Gln Tyr Glu
                195                 200                 205
Asn Leu Lys Tyr Thr Val Ile Ile Thr Val His Thr Gly Asp Gln Asn
 210                 215                 220
Gln Val Gly Asn Glu Thr Gln Gly Val Thr Val Glu Ile Thr Pro Gln
 225                 230                 235                 240
Ala Ser Thr Thr Glu Ala Ile Leu Pro Glu Tyr Gly Thr Leu Gly Leu
                245                 250                 255
Glu Cys Phe Pro Leu Thr Gly Leu Asp Phe Asn Glu Met Ile Leu Leu
                260                 265                 270
Thr Met Lys Asn Lys Ala Trp Met Val Asn Arg Gln Trp Phe Phe Asp
            275                 280                 285
Leu Pro Leu Pro Trp Thr Ser Gly Ala Thr Thr Glu Thr Pro Thr Trp
            290                 295                 300
Asn Arg Lys Glu Leu Leu Val Thr Phe Lys Ser Ala His Ala Lys Lys
 305                 310                 315                 320
Gln Glu Val Val Val Leu Gly Ser Gln Glu Gly Ala Met Ala Thr Ala
                325                 330                 335
Leu Thr Gly Ala Thr Glu Ile Gln Asn Ser Gly Gly Thr Ser Ile Phe
                340                 345                 350
Ala Gly Ala Leu Lys Cys Arg Leu Lys Met Asp Lys Leu Glu Leu Lys
                355                 360                 365
Gly Met Ser Tyr Ala Met Cys Thr Asn Thr Phe Val Leu Lys Lys Glu
            370                 375                 380
Val Ser Glu Thr Gln Ala Gly Thr Ile Leu Ile Gln Val Glu Tyr Lys
 385                 390                 395                 400
Gly Glu Asp Val Pro Cys Lys Ile Pro Phe Ser Thr Glu Asp Gly Gln
                405                 410                 415
Gly Lys Ala His Asn Gly Arg Leu Ile Thr Ala Asn Pro Val Val Thr
```

```
                    420               425               430
Lys Lys Glu Glu Pro Val Asn Ile Glu Ala Glu Pro Pro Phe Gly Glu
            435               440               445

Ser Asn Ile Val Ile Gly Ile Gly Asp Asn Ala Leu Lys Ile Asn Trp
        450               455               460

Tyr Lys Lys Gly Ser Thr Leu Gly Lys Ala Phe Ser Thr Thr Leu Lys
465               470               475               480

Gly Ala Gln Arg Leu Ala Ala Leu Gly Asp Thr Ala Trp Asp Phe Gly
            485               490               495

Ser Ile Gly Gly Val Phe Asn Ser Ile Gly Lys Ala Val His Gln Val
        500               505               510

Phe Gly Gly Ala Phe Arg Thr Leu Phe Gly Gly Met Ser Trp Ile Thr
            515               520               525

Gln Gly Leu Met Gly Ala Leu Leu Leu Trp Met Gly Val Asn Ala Arg
            530               535               540

Asp Arg Ser Ile Ala Leu Ala Phe Leu Ala Thr Gly Gly Val Leu Val
545               550               555               560

Phe Leu Ala Thr Asn Val His Ala
                565

<210> SEQ ID NO 5
<211> LENGTH: 1710
<212> TYPE: DNA
<213> ORGANISM: Dengue virus

<400> SEQUENCE: 5
agcgtggctc tggctcctgc tgtgggtctg gtctggagaa cccgcaccga gacctggatg    60
tcctccgagg gtgcttggaa gcagatccag cgcgtggaga cctgggctct gcgccaccct   120
ggtttcaccg tgatcgctct gttcctggct cacgctatcg aacctccat cacccagaag    180 ggtatcatct tcatcctgct gatgctggtg acccccttcca tggctatgcg ctgcgtgggt   240
atcggttccc gcgacttcgt ggagggtctg tccggtgcta cctgggtgga cgtggtgctg   300
gagaacggtt cctgcgtgac caccatggct aaggacaagc ctaccctgga catcgagctg   360
ctgaagaccg aggtgaccaa ccctgctgtg ctgcgcaagc tgtgcatcga ggctaagatc   420
tccaacacca ccaccgactc ccgctgccct acccagggtg aggctaccct ggtggaggag   480
caggacgcta acttcgtgtg ccgccgcacc ttcgtggacc gcggttgggg taacggttgc   540
ggtctgttcg gtaagggttc cctgctgacc tgcgctaagt tcaagtgcgt gaccaagctg   600
gagggtaaga tcgtgcagta cgagaacctg aagtactccg tgatcgtgac cgtgcacacc   660
ggtgaccaga accaggtggg taacgagtcc accgagcacg gaaccaccgc taccatcacc   720
cctcaggctc ctaccaccga gatccagctg accgactacg tgctctgac cctggactgc   780 ttccctctga ccggtctgga cttcaacgag atggtgctgc tgaccatgaa ggagaagtcc   840
tggctggtga caagcagtg gttcctggac ctgcctctgc cttggacctc cggtgcttcc   900
acctcccagg agacctggaa ccgccaggac ctgctggtga ccttcaagac cgctcacgct   960
aagaagcagg aggtggtggt gctgggttcc caggagggtg ctatggctac cgctctgacc  1020
ggtgctaccg agatccagac ctccggaacc accaccatct ccgctggtca cctgaagtgc  1080
cgcctgaaga tggacaagct gaccctgaag ggtatgtcct acgtgatgtg caccggttcc  1140
ttcaagctgg agaaggaggt ggctgagacc caggctggaa ccgtgctggt gcagatcaag  1200
tacgagggaa ccgacgctcc ttgcaagatc cctttctcca cccaggacga gaagggtgtg  1260
```

| | |
|---|---|
| acccagaacg gtcgcctgat caccgctaac cctatcgtga ccgacaagga gaagcctgtg | 1320 |
| aacatcgagg ctgagcctcc tttcggtgag tcctacatcg tgatcggtgc tggtgagaag | 1380 |
| gctctgaagc tgtcctggtt caagaagggt tccaccctgg gtaaggcttt ctccaccacc | 1440 |
| ctgaagggtg ctcagcgcct ggctgctctg ggtgacaccg cttgggactt cggttccatc | 1500 |
| ggtggtgtgt tcaactccat cggtaaggct gtgcaccagg tgttcggtgg tgctttccgc | 1560 |
| accctgttcg gtggtatgtc ctggatcacc cagggtctga tgggtgctct gctgctgtgg | 1620 |
| atgggtgtga acgctcgcga ccgctccatc gctctggctt tcctggctac cggtggtgtg | 1680 |
| ctggtgttcc tggctaccaa cgtgcacgct | 1710 |

<210> SEQ ID NO 6
<211> LENGTH: 1710
<212> TYPE: DNA
<213> ORGANISM: Dengue virus

<400> SEQUENCE: 6

| | |
|---|---|
| tccgtggctc tggtgcctgc tgtgggtatg ggtctggaga cccgcaccga gacctggatg | 60 |
| tcctccgagg gtgcttggaa gcacgctcag cgcatcgaga cctggatcct gcgccaccct | 120 |
| ggtttccacca tcatggctgc tatcctggct tacaccatcg gaaccaccca cttccagcgc | 180 |
| gtgctgatct tcatcctgct gaccgctgtg gctccttcca tgaccatgcg ctgcatcggt | 240 |
| atctccaacc gcgacttcgt ggagggtgtg tccggtggtt cctgggtgga catcgtgctg | 300 |
| gagaacggtt cctgcgtgac caccatggct aagaacaagc taccctggac cttcgagctg | 360 |
| atcaagaccg aggctaagca gcctgctacc ctgcgcaagt actgcatcga ggctaagctg | 420 |
| accaacacca ccaccgagtc ccgctgccct acccagggtg agccttccct gaaggaggag | 480 |
| caggacaagc gcttcgtgtg caagcactcc atggtggacc gcggttgggg taacggttgc | 540 |
| ggtctgttcg gtaagggtgg tatcgtgacc tgcgctatgt tcacctgcaa gaagaacatg | 600 |
| gagggtaaga tcgtgcagcc tgagaacctg gagtacacca tcgtggtgac ccctcactcc | 660 |
| ggtgaggaga acgctgtggg taacgacacc ggtaagcacg gtaaggagat caaggtgacc | 720 |
| cctcagtcct ccatcaccga ggctgagctg accggttacg gaaccgtgac catggagtgc | 780 |
| ttccctctga ccggtctgga cttcaacgag atggtgctgc tgcagatgga gaacaaggct | 840 |
| tggctggtga accgccagtg gttcctggac ctgcctctgc cttggctgcc tggtgctgac | 900 |
| aagcaggagt ccaactggat ccagaaggag accctggtga ccttcaagtc ccctcacgct | 960 |
| aagaagcagg acgtggtggt gctgggttcc caggagggtg ctatggctac cgctctgacc | 1020 |
| ggtgctaccg agatccagat gtcctccggt aacctgctgt tcaccggtgc cctgaagtgc | 1080 |
| cgcctgcgca tggacaagct gcagctgaag ggtatgtcct actccatgtg caccggtaag | 1140 |
| ttcaaggtgg tgaaggagat cgctgagacc caggctggaa ccatcgtgat ccaggtgcag | 1200 |
| tacgagggtg acggttcccc ttgcaagatc ccttttcgaga tcatggacct ggagaagcgc | 1260 |
| tacgtgctgg gtcgcctgat caccgtgaac cctatcgtga ccgagaagga ctcccctgtg | 1320 |
| aacatcgagg ctgagcctcc tttcggtgac tcctacatca tcatcggtgt ggagcctggt | 1380 |
| cagctgaagc tgaactggtt caagaagggt tccaccctgg gtaaggcttt ctccaccacc | 1440 |
| ctgaagggtg ctcagcgcct ggctgctctg ggtgacaccg cttgggactt cggttccatc | 1500 |
| ggtggtgtgt tcaactccat cggtaaggct gtgcaccagg tgttcggtgg tgctttccgc | 1560 |
| accctgttcg gtggtatgtc ctggatcacc cagggtctga tgggtgctct gctgctgtgg | 1620 |
| atgggtgtga acgctcgcga ccgctccatc gctctggctt tcctggctac cggtggtgtg | 1680 |

```
ctggtgttcc tggctaccaa cgtgcacgct                              1710
```

<210> SEQ ID NO 7
<211> LENGTH: 1710
<212> TYPE: DNA
<213> ORGANISM: Dengue virus

<400> SEQUENCE: 7

```
agcgtggctc tgacccctgc ttccggtatg ggtctggaga cccgcgctga gacctggatg    60
tcctccgagg gtgcttggaa gcacgctcag cgcgtggagt cctggatcct gcgcaaccct   120
ggtttcgctc tgctggctgg tttcatggct tacatgatcg gtcagaccgg tatccagcgc   180
accgtgttct tcgtgctgat gatgctggtg gctccttcct acggtatgcg ctgcgtgggt   240
gtgggtaacc gcgacttcgt ggagggtgtg tccggtggtg cttgggtgga cctggtgctg   300
gagaacggtg gttgcgtgac caccatggct cagggtaagc ctaccctgga cttcgagctg   360
accaagacca ccgctaagga ggtggctctg ctgcgcacct actgcatcga ggcttccatc   420
tccaacatca ccaccgctac ccgctgccct acccagggtg agccttacct gaaggaggag   480
caggaccagc agtacatctg ccgccgcgac gtggtgacc gcggttgggg taacggttgc   540
ggtctgttcg gtaagggtgg tgtggtgacc tgcgctaagt tctcctgctc cggtaagatc   600
accggtaacc tggtgcagat cgagaacctg gagtacaccg tggtggtgac cgtgcacaac   660
ggtgacacca acgctgtggg taacgacacc tccaaccacg gtgtgaccgc tatgatcacc   720
cctcgctccc cttccgtgga ggtgaagctg cctgactacg tgagctgac cctggactgc   780 ttccctctgt ccggtatcga cttcaacgag atgatcctga tgaagatgaa gaagaagacc   840
tggctggtga caagcagtg gttcctggac ctgcctctgc cttggaccgc tggtgctgac   900
acctccgagg tgcactggaa ctacaaggag cgcatggtga ccttcaagtc ccctcacgct   960
aagcgccagg acgtgaccgt gctgggttcc caggagggtg ctatggcttc cgctctggct  1020
ggtgctaccg aggtggactc cggtgacggt aaccacatgt tcgctggtgc tctgaagtgc  1080
aaggtgcgca tggagaagct gcgcatcaag ggtatgtcct acaccatgtg ctccggtaag  1140
ttctccatcg acaaggagat ggctgagacc caggctggta ctaccgtggt gcaggtgaag  1200
tacgagggtg ctggtgctcc ttgcaaggtg cctatcgaga tccgcgacgt gaacaaggag  1260
aaggtggtgg gtcgcatcat ctcctccacc cctctggctg agaacaccaa ctccgtgacc  1320
aacatcgagc tggagcctcc tttcggtgac tcctacatcg tgatcggtgt gggtaactcc  1380
gctctgaccc tgcactggtt ccgcaagggt tccaccctgg gtaaggcctt ctccaccacc  1440
ctgaagggtg ctcagcgcct ggctgctctg ggtgacaccg cttggactt cggttccatc  1500 ggtggtgtgt tcaactccat cggtaaggct gtgcaccagg tgttcggtgg tgcttccgc  1560 accctgttcg gtggtatgtc ctggatcacc cagggtctga tgggtgctct gctgctgtgg  1620
atgggtgtga acgctcgcga ccgctccatc gctctggctt cctggctac cggtggtgtg  1680 ctggtgttcc tggctaccaa cgtgcacgct                              1710
```

<210> SEQ ID NO 8
<211> LENGTH: 1707
<212> TYPE: DNA
<213> ORGANISM: Dengue virus

<400> SEQUENCE: 8

```
tcc

```
tccgctgagg gtgcttggcg tcaggtggag aaggtggaga cctgggctct gcgccaccct      120
ggtttcacca tcctggctct gttcctggct cactacatcg gcacctccct gacccagaag      180
gtggtgatct tcatcctgct gatgctggtg accccttcca tgaccatgcg ctgcgtgggt      240
gtgggtaacc gcgacttcgt ggagggtctg tccggtgcta cctgggtgga cgtggtgctg      300
gagaacggtg gttgcgtgac caccatggct aagaacaagc ctaccctgga catcgagctg      360
cagaagaccg aggctaccca gctggctacc ctgcgcaagc tgtgcatcga gggtaagatc      420
accaacatca ccaccgactc ccgctgccct acccagggtg aggctgctct gcctgaggag      480
caggaccaga actacgtgtg caagcacacc tacgtggacc gcggttgggg taacggttgc      540
ggtctgttcg gtaagggttc cctggtgacc tgcgctaagt tccagtgcct ggagcctatc      600
gagggtaagg tggtgcagta cgagaacctg aagtacaccg tgatcatcac cgtgcacacc      660
ggtgaccaga accaggtggg taacgagacc cagggtgtga ccgtggagat caccccctcag     720
gcttccacca ccgaggctat cctgcctgag tacggcaccc tgggtctgga gtgcttccct      780
ctgaccggtc tggacttcaa cgagatgatc ctgctgacca tgaagaacaa ggcttggatg      840
gtgaaccgcc agtggttctt cgacctgcct ctgccttgga cctccggtgc taccaccgag      900
accccctacct ggaaccgcaa ggagctgctg gtgaccttca gtccgctca cgctaagaag      960
caggaggtgg tggtgctggg ttcccaggag ggtgctatgg ctaccgctct gaccggtgct     1020
accgagatcc agaactccgg tggcaccctcc atcttcgctg tgctctgaa gtgccgcctg     1080
aagatggaca gctggagct gaagggtatg tcctacgcta tgtgcaccaa caccttcgtg     1140
ctgaagaag aggtgtccga cccaggct ggcaccatcc tgatccaggt ggagtacaag     1200
ggtgaggacg tgccttgcaa gatccctttc tccaccgagg acggtcaggg taaggctcac     1260
aacggtcgcc tgatcaccgc taaccctgtg gtgaccaaga aggaggagcc tgtgaacatc     1320
gaggctgagc ctccttttcgg tgagtccaac atcgtgatcg gtatcggtga caacgctctg     1380
aagatcaact ggtacaagaa gggttccacc ctgggtaagg ccttctccac caccctgaag     1440
ggtgctcagc gcctggctgc tctgggtgac accgcttggg acttcggttc catcggtggt     1500
gtgttcaact ccatcggtaa ggctgtgcac caggtgttcg gtggctgttt ccgcaccctg     1560
ttcggtggta tgtcctggat cacccagggt ctgatgggtg ctctgctgct gtggatgggt     1620
gtgaacgctc gcgaccgctc catcgctctg gctttcctgg ctaccggtgg tgtgctggtg     1680
ttcctggcta ccaacgtgca cgcttaa                                        1707
```

<210> SEQ ID NO 9
<211> LENGTH: 570
<212> TYPE: PRT
<213> ORGANISM: Dengue virus

<400> SEQUENCE: 9

```
Ser Val Ala Leu Ala Pro His Val Gly Leu Gly Leu Glu Thr Arg Thr
1               5                   10                  15

Glu Thr Trp Met Ser Ser Glu Gly Ala Trp Lys Gln Ile Gln Lys Val
            20                  25                  30

Glu Thr Trp Ala Leu Arg His Pro Gly Phe Thr Val Ile Ala Leu Phe
        35                  40                  45

Leu Ala His Ala Ile Gly Thr Ser Ile Thr Gln Lys Gly Ile Ile Phe
    50                  55                  60

Ile Leu Leu Met Leu Val Thr Pro Ser Met Ala Met Arg Cys Val Gly
65                  70                  75                  80
```

```
Ile Gly Asn Arg Asp Phe Val Glu Gly Leu Ser Gly Ala Thr Trp Val
                85                  90                  95

Asp Val Val Leu Glu His Gly Ser Cys Val Thr Thr Met Ala Lys Asp
            100                 105                 110

Lys Pro Thr Leu Asp Ile Glu Leu Leu Lys Thr Glu Val Thr Asn Pro
        115                 120                 125

Ala Val Leu Arg Lys Leu Cys Ile Glu Ala Lys Ile Ser Asn Thr Thr
    130                 135                 140

Thr Asp Ser Arg Cys Pro Thr Gln Gly Glu Ala Thr Leu Val Glu Glu
145                 150                 155                 160

Gln Asp Thr Asn Phe Val Cys Arg Arg Thr Phe Val Asp Arg Gly Trp
                165                 170                 175

Gly Asn Gly Cys Gly Leu Phe Gly Lys Gly Ser Leu Ile Thr Cys Ala
            180                 185                 190

Lys Phe Lys Cys Val Thr Lys Leu Glu Gly Lys Ile Val Gln Tyr Glu
        195                 200                 205

Asn Leu Lys Tyr Ser Val Ile Val Thr Val His Thr Gly Asp Gln His
    210                 215                 220

Gln Val Gly Asn Glu Thr Thr Glu His Gly Thr Thr Ala Thr Ile Thr
225                 230                 235                 240

Pro Gln Ala Pro Thr Ser Glu Ile Gln Leu Thr Asp Tyr Gly Ala Leu
                245                 250                 255

Thr Leu Asp Cys Ser Pro Arg Thr Gly Leu Asp Phe Asn Glu Met Val
            260                 265                 270

Leu Leu Thr Met Glu Lys Lys Ser Trp Leu Val His Lys Gln Trp Phe
        275                 280                 285

Leu Asp Leu Pro Leu Pro Trp Thr Ser Gly Ala Ser Thr Ser Gln Glu
    290                 295                 300

Thr Trp Asn Arg Gln Asp Leu Leu Val Thr Phe Lys Thr Ala His Ala
305                 310                 315                 320

Lys Lys Gln Glu Val Val Val Leu Gly Ser Gln Glu Gly Ala Met His
                325                 330                 335

Thr Ala Leu Thr Gly Ala Thr Glu Ile Gln Thr Ser Gly Thr Thr Thr
            340                 345                 350

Ile Phe Ala Gly His Leu Lys Cys Arg Leu Lys Met Asp Lys Leu Thr
        355                 360                 365

Leu Lys Gly Met Ser Tyr Val Met Cys Thr Gly Ser Phe Lys Leu Glu
    370                 375                 380

Lys Glu Val Ala Glu Thr Gln His Gly Thr Val Leu Val Gln Val Lys
385                 390                 395                 400

Tyr Glu Gly Thr Asp Ala Pro Cys Lys Ile Pro Phe Ser Ser Gln Asp
                405                 410                 415

Glu Lys Gly Val Thr Gln Asn Gly Arg Leu Ile Thr Ala Asn Pro Ile
            420                 425                 430

Val Thr Asp Lys Glu Lys Pro Val Asn Ile Glu Ala Glu Pro Pro Phe
        435                 440                 445

Gly Glu Ser Tyr Ile Val Val Gly Ala Gly Glu Lys Ala Leu Lys Leu
    450                 455                 460

Ser Trp Phe Lys Lys Gly Ser Thr Leu Gly Lys Ala Phe Ser Thr Thr
465                 470                 475                 480

Leu Lys Gly Ala Gln Arg Leu Ala Ala Leu Gly Asp Thr Ala Trp Asp
                485                 490                 495

Phe Gly Ser Ile Gly Gly Val Phe Asn Ser Ile Gly Lys Ala Val His
```

```
                500                 505                 510
    Gln Val Phe Gly Gly Ala Phe Arg Thr Leu Phe Gly Gly Met Ser Trp
                515                 520                 525
    Ile Thr Gln Gly Leu Met Gly Ala Leu Leu Leu Trp Met Gly Val Asn
                530                 535                 540
    Ala Arg Asp Arg Ser Ile Ala Leu Ala Phe Leu Ala Thr Gly Gly Val
    545                 550                 555                 560
    Leu Val Phe Leu Ala Thr Asn Val His Ala
                565                 570

<210> SEQ ID NO 10
<211> LENGTH: 570
<212> TYPE: PRT
<213> ORGANISM: Dengue virus

<400> SEQUENCE: 10

Ser Val Ala Leu Val Pro His Val Gly Met Gly Leu Glu Thr Arg Thr
    1               5                   10                  15
    Glu Thr Trp Met Ser Ser Glu Gly Ala Trp Lys His Val Gln Arg Ile
                20                  25                  30
    Glu Thr Trp Ile Leu Arg His Pro Gly Phe Thr Met Met Ala Ala Ile
                35                  40                  45
    Leu Ala Tyr Thr Ile Gly Thr Thr His Phe Gln Arg Ala Leu Ile Phe
    50                  55                  60
    Ile Leu Leu Thr Ala Val Thr Pro Ser Met Thr Met Arg Cys Ile Gly
    65                  70                  75                  80
    Met Ser Asn Arg Asp Phe Val Glu Gly Val Ser Gly Gly Ser Trp Val
                85                  90                  95
    Asp Ile Val Leu Glu His Gly Ser Cys Val Thr Thr Met Ala Lys Asn
                100                 105                 110
    Lys Pro Thr Leu Asp Phe Glu Leu Ile Lys Thr Glu Ala Lys Gln Pro
                115                 120                 125
    Ala Thr Leu Arg Lys Tyr Cys Ile Glu Ala Lys Leu Thr Asn Thr Thr
    130                 135                 140
    Thr Glu Ser Arg Cys Pro Thr Gln Gly Glu Pro Ser Leu Asn Glu Glu
    145                 150                 155                 160
    Gln Asp Lys Arg Phe Val Cys Lys His Ser Met Val Asp Arg Gly Trp
                165                 170                 175
    Gly Asn Gly Cys Gly Leu Phe Gly Lys Gly Ile Val Thr Cys Ala
                180                 185                 190
    Met Phe Arg Cys Lys Lys Asn Met Glu Gly Lys Val Val Gln Pro Glu
                195                 200                 205
    Asn Leu Glu Tyr Thr Ile Val Ile Thr Pro His Ser Gly Glu Glu His
    210                 215                 220
    Ala Val Gly Asn Asp Thr Gly Lys His Gly Lys Glu Ile Lys Ile Thr
    225                 230                 235                 240
    Pro Gln Ser Ser Ile Thr Glu Ala Glu Leu Thr Gly Tyr Gly Thr Val
                245                 250                 255
    Thr Met Glu Cys Ser Pro Arg Thr Gly Leu Asp Phe Asn Glu Met Val
                260                 265                 270
    Leu Leu Gln Met Glu Asn Lys Ala Trp Leu Val His Arg Gln Trp Phe
                275                 280                 285
    Leu Asp Leu Pro Leu Pro Trp Leu Pro Gly Ala Asp Thr Gln Gly Ser
                290                 295                 300
```

```
Asn Trp Ile Gln Lys Glu Thr Leu Val Thr Phe Lys Asn Pro His Ala
305                 310                 315                 320

Lys Lys Gln Asp Val Val Leu Gly Ser Gln Glu Gly Ala Met His
            325                 330                 335

Thr Ala Leu Thr Gly Ala Thr Glu Ile Gln Met Ser Ser Gly Asn Leu
            340                 345                 350

Leu Phe Thr Gly His Leu Lys Cys Arg Leu Arg Met Asp Lys Leu Gln
            355                 360                 365

Leu Lys Gly Met Ser Tyr Ser Met Cys Thr Gly Lys Phe Lys Val Val
            370                 375                 380

Lys Glu Ile Ala Glu Thr Gln His Gly Thr Ile Val Ile Arg Val Gln
385                 390                 395                 400

Tyr Glu Gly Asp Gly Ser Pro Cys Lys Ile Pro Phe Glu Ile Met Asp
                405                 410                 415

Leu Glu Lys Arg His Val Leu Gly Arg Leu Ile Thr Val Asn Pro Ile
            420                 425                 430

Val Thr Glu Lys Asp Ser Pro Val Asn Ile Glu Ala Glu Pro Pro Phe
            435                 440                 445

Gly Asp Ser Tyr Ile Ile Ile Gly Val Glu Pro Gly Gln Leu Lys Leu
450                 455                 460

Asn Trp Phe Lys Lys Gly Ser Thr Leu Gly Lys Ala Phe Ser Thr Thr
465                 470                 475                 480

Leu Lys Gly Ala Gln Arg Leu Ala Ala Leu Gly Asp Thr Ala Trp Asp
                485                 490                 495

Phe Gly Ser Ile Gly Gly Val Phe Asn Ser Ile Gly Lys Ala Val His
            500                 505                 510

Gln Val Phe Gly Gly Ala Phe Arg Thr Leu Phe Gly Gly Met Ser Trp
            515                 520                 525

Ile Thr Gln Gly Leu Met Gly Ala Leu Leu Leu Trp Met Gly Val Asn
530                 535                 540

Ala Arg Asp Arg Ser Ile Ala Leu Ala Phe Leu Ala Thr Gly Gly Val
545                 550                 555                 560

Leu Val Phe Leu Ala Thr Asn Val His Ala
                565                 570

<210> SEQ ID NO 11
<211> LENGTH: 570
<212> TYPE: PRT
<213> ORGANISM: Dengue virus

<400> SEQUENCE: 11

Ser Val Ala Leu Thr Pro His Ser Gly Met Gly Leu Glu Thr Arg Ala
1               5                   10                  15

Glu Thr Trp Met Ser Ser Glu Gly Ala Trp Lys His Ala Gln Arg Val
                20                  25                  30

Glu Ser Trp Ile Leu Arg Asn Pro Gly Phe Ala Leu Leu Ala Gly Phe
            35                  40                  45

Met Ala Tyr Met Ile Gly Gln Thr Gly Ile Gln Arg Thr Val Phe Phe
50                  55                  60

Val Leu Met Met Leu Val Ala Pro Ser Tyr Gly Met Arg Cys Val Gly
65                  70                  75                  80

Val Gly Asn Arg Asp Phe Val Glu Gly Val Ser Gly Gly Ala Trp Val
                85                  90                  95

Asp Leu Val Leu Glu His Gly Gly Cys Val Thr Thr Met Ala Gln Gly
            100                 105                 110
```

```
Lys Pro Thr Leu Asp Phe Glu Leu Ile Lys Thr Thr Ala Lys Glu Val
            115                 120                 125

Ala Leu Leu Arg Thr Tyr Cys Ile Glu Ala Ser Ile Ser Asn Ile Thr
130                 135                 140

Thr Ala Thr Arg Cys Pro Thr Gln Gly Glu Pro Tyr Leu Lys Glu Glu
145                 150                 155                 160

Gln Asp Gln Gln Tyr Ile Cys Arg Arg Asp Val Val Asp Arg Gly Trp
                165                 170                 175

Gly Asn Gly Cys Gly Leu Phe Gly Lys Gly Val Val Thr Cys Ala
            180                 185                 190

Lys Phe Ser Cys Ser Gly Lys Ile Thr Gly Asn Leu Val Gln Ile Glu
            195                 200                 205

Asn Leu Glu Tyr Thr Val Val Val Thr Val His Asn Gly Asp Thr His
            210                 215                 220

Ala Val Gly Asn Asp Ile Ser Asn His Gly Val Thr Ala Thr Ile Thr
225                 230                 235                 240

Pro Arg Ser Pro Ser Val Glu Val Lys Leu Pro Asp Tyr Gly Glu Leu
                245                 250                 255

Thr Leu Asp Cys Glu Pro Arg Ser Gly Ile Asp Phe Asn Glu Met Ile
            260                 265                 270

Leu Met Lys Met Lys Lys Lys Thr Trp Leu Val His Lys Gln Trp Phe
            275                 280                 285

Leu Asp Leu Pro Leu Pro Trp Ala Ala Gly Ala Asp Thr Ser Glu Val
            290                 295                 300

His Trp Asn Tyr Lys Glu Arg Met Val Thr Phe Lys Val Pro His Ala
305                 310                 315                 320

Lys Arg Gln Asp Val Thr Val Leu Gly Ser Gln Glu Gly Ala Met His
                325                 330                 335

Ser Ala Leu Thr Gly Ala Thr Glu Val Asp Ser Gly Asp Gly Asn His
            340                 345                 350

Met Phe Ala Gly His Leu Lys Cys Lys Val Arg Met Glu Lys Leu Arg
            355                 360                 365

Ile Lys Gly Met Ser Tyr Thr Met Cys Ser Gly Lys Phe Ser Ile Asp
            370                 375                 380

Lys Glu Met Ala Glu Thr Gln His Gly Thr Thr Val Val Lys Val Lys
385                 390                 395                 400

Tyr Glu Gly Ala Gly Ala Pro Cys Lys Val Pro Ile Glu Ile Arg Asp
                405                 410                 415

Val Asn Lys Glu Lys Val Val Gly Arg Ile Ile Ser Ser Thr Pro Phe
            420                 425                 430

Ala Glu Tyr Thr Asn Ser Val Thr Asn Ile Glu Leu Glu Pro Pro Phe
            435                 440                 445

Gly Asp Ser Tyr Ile Val Ile Gly Val Gly Asp Ser Ala Leu Thr Leu
450                 455                 460

His Trp Phe Arg Lys Gly Ser Thr Leu Gly Lys Ala Phe Ser Thr Thr
465                 470                 475                 480

Leu Lys Gly Ala Gln Arg Leu Ala Ala Leu Gly Asp Thr Ala Trp Asp
                485                 490                 495

Phe Gly Ser Ile Gly Gly Val Phe Asn Ser Ile Gly Lys Ala Val His
            500                 505                 510

Gln Val Phe Gly Gly Ala Phe Arg Thr Leu Phe Gly Gly Met Ser Trp
            515                 520                 525
```

Ile Thr Gln Gly Leu Met Gly Ala Leu Leu Leu Trp Met Gly Val Asn
530                 535                 540

Ala Arg Asp Arg Ser Ile Ala Leu Ala Phe Leu Ala Thr Gly Gly Val
545                 550                 555                 560

Leu Val Phe Leu Ala Thr Asn Val His Ala
                565                 570

<210> SEQ ID NO 12
<211> LENGTH: 568
<212> TYPE: PRT
<213> ORGANISM: Dengue virus

<400> SEQUENCE: 12

Ser Val Ala Leu Ala Pro His Val Gly Met Gly Leu Asp Thr Arg Thr
1               5                   10                  15

Gln Thr Trp Met Ser Ala Glu Gly Ala Trp Arg Gln Val Glu Lys Val
            20                  25                  30

Glu Thr Trp Ala Leu Arg His Pro Gly Phe Thr Ile Leu Ala Leu Phe
        35                  40                  45

Leu Ala His Tyr Ile Gly Thr Ser Leu Thr Gln Lys Val Val Ile Phe
    50                  55                  60

Ile Leu Leu Met Leu Val Thr Pro Ser Met Thr Met Arg Cys Val Gly
65                  70                  75                  80

Val Gly Asn Arg Asp Phe Val Glu Gly Leu Ser Gly Ala Thr Trp Val
                85                  90                  95

Asp Val Val Leu Glu His Gly Gly Cys Val Thr Thr Met Ala Lys Asn
            100                 105                 110

Lys Pro Thr Leu Asp Ile Glu Leu Gln Lys Thr Glu Ala Thr Gln Leu
        115                 120                 125

Ala Thr Leu Arg Lys Leu Cys Ile Glu Gly Lys Ile Thr Asn Ile Thr
    130                 135                 140

Thr Asp Ser Arg Cys Pro Thr Gln Gly Glu Ala Ile Leu Pro Glu Glu
145                 150                 155                 160

Gln Asp Gln Asn Tyr Val Cys Lys His Thr Tyr Val Asp Arg Gly Trp
                165                 170                 175

Gly Asn Gly Cys Gly Leu Phe Gly Lys Gly Ser Leu Val Thr Cys Ala
            180                 185                 190

Lys Phe Gln Cys Leu Glu Ser Ile Glu Gly Lys Val Val Gln His Glu
        195                 200                 205

Asn Leu Lys Tyr Thr Val Ile Ile Thr Val His Thr Gly Asp Gln His
    210                 215                 220

Gln Val Gly Asn Glu Thr Gln Gly Val Thr Ala Glu Ile Thr Pro Gln
225                 230                 235                 240

Ala Ser Thr Ala Glu Val Ile Leu Pro Glu Tyr Gly Thr Leu Gly Leu
                245                 250                 255

Glu Cys Ser Pro Arg Thr Gly Leu Asp Phe Asn Glu Met Ile Ser Leu
            260                 265                 270

Thr Met Lys Asn Lys Ala Trp Met Val His Arg Gln Trp Phe Phe Asp
        275                 280                 285

Leu Pro Leu Pro Trp Thr Ser Gly Ala Thr Ala Glu Thr Pro Thr Trp
    290                 295                 300

Asn Arg Lys Glu Leu Leu Val Thr Phe Lys Asn Ala His Ala Lys Lys
305                 310                 315                 320

Gln Glu Val Val Val Leu Gly Ser Gln Glu Gly Ala Met His Thr Ala
                325                 330                 335

Leu Thr Gly Ala Thr Glu Ile Gln Thr Ser Gly Thr Ser Ile Phe
                340                 345                 350

Ala Gly His Leu Lys Cys Arg Leu Lys Met Asp Lys Leu Glu Leu Lys
            355                 360                 365

Gly Met Ser Tyr Ala Met Cys Leu Ser Ser Phe Val Leu Lys Lys Glu
        370                 375                 380

Val Ser Glu Thr Gln His Gly Thr Ile Leu Ile Lys Val Glu Tyr Lys
385                 390                 395                 400

Gly Glu Asp Ala Pro Cys Lys Ile Pro Phe Ser Thr Glu Asp Gly Gln
                405                 410                 415

Gly Lys Ala His Asn Gly Arg Leu Ile Thr Ala Asn Pro Val Val Thr
            420                 425                 430

Lys Lys Glu Glu Pro Val Asn Ile Glu Ala Glu Pro Pro Phe Gly Glu
        435                 440                 445

Ser Asn Ile Val Ile Gly Ile Gly Asp Lys Ala Leu Lys Ile Asn Trp
450                 455                 460

Tyr Lys Lys Gly Ser Thr Leu Gly Lys Ala Phe Ser Thr Thr Leu Lys
465                 470                 475                 480

Gly Ala Gln Arg Leu Ala Ala Leu Gly Asp Thr Ala Trp Asp Phe Gly
                485                 490                 495

Ser Ile Gly Gly Val Phe Asn Ser Ile Gly Lys Ala Val His Gln Val
            500                 505                 510

Phe Gly Gly Ala Phe Arg Thr Leu Phe Gly Gly Met Ser Trp Ile Thr
        515                 520                 525

Gln Gly Leu Met Gly Ala Leu Leu Leu Trp Met Gly Val Asn Ala Arg
530                 535                 540

Asp Arg Ser Ile Ala Leu Ala Phe Leu Ala Thr Gly Gly Val Leu Val
545                 550                 555                 560

Phe Leu Ala Thr Asn Val His Ala
                565

<210> SEQ ID NO 13
<211> LENGTH: 99
<212> TYPE: PRT
<213> ORGANISM: Japanese encephalitis virus

<400> SEQUENCE: 13

Thr Leu Gly Lys Ala Phe Ser Thr Thr Leu Lys Gly Ala Gln Arg Leu
1               5                   10                  15

Ala Ala Leu Gly Asp Thr Ala Trp Asp Phe Gly Ser Ile Gly Gly Val
            20                  25                  30

Phe Asn Ser Ile Gly Lys Ala Val His Gln Val Phe Gly Gly Ala Phe
        35                  40                  45

Arg Thr Leu Phe Gly Gly Met Ser Trp Ile Thr Gln Gly Leu Met Gly
    50                  55                  60

Ala Leu Leu Leu Trp Met Gly Val Asn Ala Arg Asp Arg Ser Ile Ala
65                  70                  75                  80

Leu Ala Phe Leu Ala Thr Gly Gly Val Leu Val Phe Leu Ala Thr Asn
                85                  90                  95

Val His Ala

The invention claimed is:

1. A virus-like particle capable of eliciting an immune response in a mammal comprising a polypeptide, wherein the polypeptide comprises modified forms of both membrane (M) and envelope (E) structural proteins of a flavivirus, wherein the flavivirus comprises a dengue virus and a Japanese encephalitis virus, wherein the E structural protein of the dengue virus is fused to a peptide of the Japanese encephalitis virus; and
   wherein the modified forms of both the M and E structural proteins comprise one or more amino acid substitutions, wherein the one or more amino acid substitutions comprise a His to Ala substitution at one or more positions corresponding to H7, H336, H357, and H392 of SEQ ID NO: 9-11, or a His to Ala substitution at one or more positions corresponding to H7, H334, H355, and H390 of SEQ ID NO: 12.

2. The virus-like particle of claim 1, wherein the flavivirus is dengue virus, Japanese encephalitis virus, Yellow fever virus, West Nile virus, or Zika virus.

3. The virus-like particle of claim 1, wherein the modified form further comprises a His to Asn substitution at one or more positions corresponding to H102, H224, and H284 in SEQ ID NO: 9-11 or a His to Asn substitution at one or more positions corresponding to positions H102, H224, and H282 in SEQ ID NO: 12.

4. The virus-like particle of claim 1, wherein the modified form further comprises one or more of: a Ser or Glu to Phe substitution at position 261 in SEQ ID NO: 9-11 or a Ser to Phe substitution at position S259 in SEQ ID NO: 12, respectively: or an Arg to Leu substitution at position R263 in SEQ ID NO: 9-11 or an Arg to Leu substitution at position R261 in SEQ ID NO: 12, respectively: an Asn or Val to Ser substitution at position 317 in SEQ ID NO: 10-11 or a Asn to Ser substitution at position N315 in SEQ ID NO: 12: or an Arg or Lys to Gln substitution at position 398 of SEQ ID NO: 10-11 or a Lys to Gln substitution at position K396 of SEQ ID NO: 12.

5. An isolated polynucleotide encoding a virus-like particle or polypeptide capable of eliciting immune response in a subject upon administrating the virus-like particle or polypeptide to the subject at a pharmaceutically effective dosage, the virus-like particle or polypeptide comprising a modified form of both membrane (M) and envelope (E) structural proteins of a dengue virus fused to a peptide from a Japanese encephalitis virus, wherein a nucleotide sequence of the modified form corresponds to a sequence set forth in SEQ ID NO: 5, SEQ ID NO: 6, SEQ ID NO: 7 or SEQ ID NO: 8, or an amino acid sequence of the modified form corresponds to a sequence set forth in SEQ ID NO: 9-12, wherein SEQ ID NO: 9-11 comprise one or more His to Ala substitutions at positions H7, H336, H357, and H392 or SEQ ID NO: 12 comprises one or more His to Ala substitutions at positions H7, H334, H355 and H390.

6. The isolated polynucleotide of claim 5, wherein the modified form further comprises a His to Asn substitution at one or more positions H102, H224, and H284 in SEQ ID NO: 9-11 or a His to Asn substitution at one or more of positions H102, H224, and H282 in SEQ ID NO: 12.

7. The isolated polynucleotide of claim 5, wherein the modified form further comprises one or more of a Ser or Glu to Phe substitution at position 261 of SEQ ID NO: 9-11 or a Ser to Phe substitution at position S259 of SEQ ID NO: 12, respectively, or an Arg to Leu substitution at position R263 in SEQ ID NO: 9-11, or an Arg to Leu substitution at position R261 in SEQ ID NO: 12, respectively, or Asn or Val to Ser substitution at position 317 in SEQ ID NO: 10-11 or a Asn to Ser substitution at position N315 in SEQ ID NO: 12, or an Arg or Lys to Gln substitution at position 398 of SEQ ID NO: 10-11 or a Lys to Gln substitution at position K396 of SEQ ID NO: 12.

8. A vaccine composition comprising: pharmaceutically acceptable adjuvant; and polypeptides or virus-like particles, which are immunologically active upon administrating to a subject, having an amino acids sequence corresponding to SEQ ID NO: 9, SEQ ID NO: 10, SEQ ID NO: 11, or SEQ ID NO: 12, wherein the amino acids sequence comprises a modified form of dengue virus sequence comprising a His to Ala substitution at one or more of positions H7, H336, H357, and H392 in SEQ ID NO: 9-11, or a His to Ala substitution at one or more of positions H7, H334, H355, and H390 in SEQ ID NO: 12.

9. The vaccine composition of claim 8, wherein the modification further comprises His to Asn substitutions at one or more positions of H102, H224, and H284 in SEQ ID NO: 9-11 or replacement of conserved amino acid His at positions E27, E149 and E207 of dengue virus sequence with amino acid Asn at positions H102, H224, and H282 in SEQ ID NO: 12.

10. The vaccine composition of claim 8, wherein the modifications further comprises one or more of a Ser or Glu to Phe substitution at position 261 in SEQ ID NO: 9-11 or a Ser to Phe substitution at position S259 in SEQ ID NO: 12, respectively, or an Arg to Leu substitution at position R263 in SEQ ID NO:9-11 or an Arg to Leu substitution at position R261 in SEQ ID NO: 12, respectively, or an Asn or Val to Ser Substitution at position 317 in SEQ ID NO: 10-11 or a Asn to Ser substitution at position N315 in SEQ ID NO: 12, or an Arg or Lys to Gln substitution at position 398 of SEQ ID NO: 10-11 or a Lys to Gln substitution at position K396 of SEQ ID NO: 12.

11. A vaccine composition comprising a pharmaceutically acceptable adjuvant and either a nucleic acid or polypeptide, wherein the nucleic acid comprises a nucleotide sequence as set forth in SEQ ID NO: 5, SEQ ID NO: 6, SEQ ID NO: 7 or SEQ ID NO: 8, respectively, or wherein the polypeptide comprises a sequence as set forth in SEQ ID NO: 1, SEQ ID NO: 2, SEQ ID NO: 3 and SEQ ID NO: 4.

* * * * *